US011229372B2

(12) United States Patent
Tao et al.

(10) Patent No.: US 11,229,372 B2
(45) Date of Patent: Jan. 25, 2022

(54) SYSTEMS AND METHODS FOR COMPUTER MONITORING OF REMOTE PHOTOPLETHYSMOGRAPHY BASED ON CHROMATICITY IN A CONVERTED COLOR SPACE

(71) Applicant: ARIZONA BOARD OF REGENTS ON BEHALF OF ARIZONA STATE UNIVERSITY, Scottsdale, AZ (US)

(72) Inventors: Nongjian Tao, Fountain Hills, AZ (US); Yuting Yang, Hangzhou (CN)

(73) Assignee: Arizona Board of Regents on Behalf of Arizona State of University, Tempe, AZ (US)

(*) Notice: Subject to any disclaimer, the term of this patent is extended or adjusted under 35 U.S.C. 154(b) by 0 days.

(21) Appl. No.: 16/335,480

(22) PCT Filed: Sep. 21, 2017

(86) PCT No.: PCT/US2017/052744
§ 371 (c)(1),
(2) Date: Mar. 21, 2019

(87) PCT Pub. No.: WO2018/057753
PCT Pub. Date: Mar. 29, 2018

(65) Prior Publication Data
US 2019/0239761 A1    Aug. 8, 2019

Related U.S. Application Data

(60) Provisional application No. 62/397,530, filed on Sep. 21, 2016.

(51) Int. Cl.
*A61B 5/02* (2006.01)
*A61B 5/024* (2006.01)
(Continued)

(52) U.S. Cl.
CPC ........ *A61B 5/02416* (2013.01); *A61B 5/0077* (2013.01); *A61B 5/0806* (2013.01);
(Continued)

(58) Field of Classification Search
CPC . A61B 5/02416; A61B 5/0077; A61B 5/0806; A61B 2576/00; G06T 5/50;
(Continued)

(56) References Cited

U.S. PATENT DOCUMENTS 7,018,338 B2    3/2006    Vetter et al.
7,336,982 B2    2/2008    Yoo
(Continued)

FOREIGN PATENT DOCUMENTS

EP    2960862 A1    12/2015
EP    2898477 B1    7/2018
(Continued)

OTHER PUBLICATIONS

Author Unknown, "AVT PIKE F-032B/F-032C AVT PIKE F-032B/F-032C fiber," Aug. 2007, Allied Vision Technologies GMBH, 2 pages.
(Continued)

*Primary Examiner* — Qian Yang
(74) *Attorney, Agent, or Firm* — Polsinelli PC

(57) ABSTRACT

Provided herein are systems and methods for computer monitoring of remote photoplethysmography (rPPG) from camera images based on chromaticity in a converted color space, which reduces motion-induced artifacts in camera images for improved rPPG computer monitoring of physiological parameters. In particular, a rPPG system for monitoring at least one physiological parameter from image data is disclosed herein. A processor subsystem electronically receives a first image data set representative of a series of consecutive images of at least a portion of a living body. The
(Continued)

processor subsystem converts the first image data set from a first color space to a second color space to generate a second image data set including first channel data comprising a luminance component and second channel data comprising a chromatic component. The processor subsystem processes the second channel data to monitor the at least one physiological parameter of the living body.

19 Claims, 16 Drawing Sheets

(51) Int. Cl.
| | |
|---|---|
| G06T 7/20 | (2017.01) |
| G06T 5/50 | (2006.01) |
| G06T 7/00 | (2017.01) |
| G06T 7/33 | (2017.01) |
| A61B 5/00 | (2006.01) |
| G06T 5/40 | (2006.01) |
| A61B 5/08 | (2006.01) |
| H04N 9/73 | (2006.01) |

(52) U.S. Cl.
CPC ............... *G06T 5/40* (2013.01); *G06T 5/50* (2013.01); *G06T 7/00* (2013.01); *G06T 7/0012* (2013.01); *G06T 7/0016* (2013.01); *G06T 7/20* (2013.01); *G06T 7/33* (2017.01); *H04N 9/735* (2013.01); *A61B 2576/00* (2013.01); *G06T 2207/10016* (2013.01); *G06T 2207/10024* (2013.01); *G06T 2207/30076* (2013.01)

(58) Field of Classification Search
CPC ........... G06T 7/0016; G06T 7/33; G06T 7/00; G06T 5/40; G06T 7/0012; G06T 7/20; G06T 2207/10024; G06T 2207/30076; G06T 2207/10016; H04N 9/735; G16H 30/40

See application file for complete search history.

(56) References Cited

U.S. PATENT DOCUMENTS

| | | | |
|---|---|---|---|
| 8,416,417 | B2 | 4/2013 | Foley et al. |
| 8,545,683 | B2 | 10/2013 | Tao et al. |
| 8,668,874 | B2 | 3/2014 | Tao et al. |
| 9,581,561 | B2 | 2/2017 | Tao et al. |
| 9,615,749 | B2 | 4/2017 | Clifton et al. |
| 9,909,993 | B2 | 3/2018 | Tao et al. |
| 10,078,074 | B2 | 9/2018 | Tsow et al. |
| 10,078,795 | B2 | 9/2018 | Tao et al. |
| 10,143,401 | B2 | 12/2018 | Tao et al. |
| 10,209,232 | B2 | 2/2019 | Forzani et al. |
| 10,222,372 | B2 | 3/2019 | Tao et al. |
| 10,398,353 | B2 * | 9/2019 | Addison ............. A61B 5/0077 |
| 10,401,298 | B2 | 9/2019 | Tao et al. |
| 10,408,757 | B2 | 9/2019 | Tao et al. |
| 10,413,226 | B2 | 9/2019 | Tao et al. |
| 2011/0293179 | A1 * | 12/2011 | Dikmen ................. G06T 5/008 382/167 |
| 2013/0115137 | A1 | 5/2013 | Tao et al. |
| 2013/0271591 | A1 | 10/2013 | Van Leest et al. |
| 2014/0275832 | A1 | 9/2014 | Muehlsteff et al. |
| 2014/0276104 | A1 | 9/2014 | Tao et al. |
| 2018/0140255 | A1 | 5/2018 | Tao et al. |
| 2019/0082972 | A1 | 3/2019 | Tao et al. |
| 2019/0094146 | A1 | 3/2019 | Tao et al. |
| 2019/0170748 | A1 | 6/2019 | Tao et al. |
| 2019/0239761 | A1 | 8/2019 | Tao et al. |
| 2019/0257802 | A1 | 8/2019 | Forzani et al. |
| 2019/0325257 | A1 | 10/2019 | Tao et al. |

FOREIGN PATENT DOCUMENTS

| | | |
|---|---|---|
| WO | 2008021614 A2 | 2/2008 |
| WO | 2009132262 A1 | 10/2009 |
| WO | 2010030874 A1 | 3/2010 |
| WO | 2010036940 A2 | 4/2010 |
| WO | 2010141610 A1 | 12/2010 |
| WO | 2011140239 A2 | 11/2011 |
| WO | 2013019843 A2 | 2/2013 |
| WO | 2014020463 A1 | 2/2014 |
| WO | 2014116604 A1 | 7/2014 |
| WO | 2015102902 A2 | 7/2015 |
| WO | 2015103459 A1 | 7/2015 |
| WO | 2017156084 A2 | 9/2017 |
| WO | 2018057753 A1 | 3/2018 |
| WO | 2018170009 A1 | 9/2018 |
| WO | 2018213790 A2 | 11/2018 |
| WO | 2019136097 A1 | 7/2019 |

OTHER PUBLICATIONS

Bashkatov, A.N., et al., "Optical properties of human skin, subcutaneous and mucous tissues in the wavelength range from 400 to 2000 nm," Journal of Physics D: Applied Physics, vol. 38, No. 15, 2005, IOP Publishing Ltd., pp. 2543-2555.

Blackford, E.B. et al., "Effects of frame rate and image resolution on pulse rate measured using multiple camera imaging photoplethysmography," Proceedings of SPIE, vol. 9417 94172D-1, Medical Imaging 2015: Biomedical Applications in Molecular, Structural, and Functional Imaging, SPIE, 14 pages.

De Haan, G. et al., "Robust Pulse Rate From Chrominance-Based rPPG," IEEE Transactions on Biomedical Engineering, vol. 60, No. 10, Oct. 2013, IEEE, pp. 2878-2886.

Estepp, J.R. et al., "Recovering pulse rate during motion artifact with a multi-imager array for non-contact imaging photoplethysmography," 2014 IEEE International Conference on Systems, Man, and Cybernetics (SMC), Oct. 5-8, 2014, San Diego, CA, USA, IEEE, pp. 1462-1469.

Feng, L., et al., "Dynamic ROI based on K-means for remote photoplethysmography," 2015 IEEE International Conference on Acoustics, Speech and Signal Processing (ICASSP), Apr. 19-24, 2015, South Brisbane, Queensland, Australia, IEEE, pp. 1310-1314.

Feng, L., et al., "Motion Artifacts Suppression for Remote Imaging Photoplethysmography," Proceedings of the 19th International Conference on Digital Signal Processing (DSP), Aug. 20-23, 2014, IEEE, pp. 18-23.

Feng, L., et al., "Motion-Resistant Remote Imaging Photoplethysmography Based on the Optical Properties of Skin," IEEE Transactions on Circuits and Systems for Video Technology, vol. 25, No. 5, May 2015, IEEE, pp. 879-891.

Garbey, M., et al., "Contact-free measurement of cardiac pulse based on the analysis of thermal imagery," IEEE Transactions on Biomedical Engineering, vol. 54, No. 8, Aug. 2007, IEEE, pp. 1418-1426.

Gupta, O. et al., "Real-Time Physiological Measurement and Visualization Using a Synchronized Multi-Camera System," 2016 IEEE Conference on Computer Vision and Pattern Recognition Workshops (CVPRW), Jun. 26-Jul. 1, 2016, Las Vegas, NV, USA, IEEE Computer Society, pp. 312-319.

Haque, M.A., et al., "Heartbeat Rate Measurement from Facial Video," IEEE Intelligent Systems, May/Jun. 2016, pp. 40-48.

Hulsbusch, M. et al., "Ein bildgestütztes, funktionelles Verfahren zur optoelektronischen Erfassung der Hautperfusion," RWTH Aachen University, 2008, Aachen, Germany, p. 70.

Lewandowska, M. et al., "Measuring Pulse Rate with a Webcam—a Non-contact Method for Evaluating Cardiac Activity," Proceedings of the Federated Conference on Computer Science and Information Systems (FedCSIS), Sep. 18-21, 2011, Szczecin, Poland, IEEE, pp. 405-410.

Lucas, B.D. et al., "An iterative image registration technique with an application to stereo vision," Proceedings of the 7th International Joint Conference on Artificial Intelligence (IJCAI), Aug. 24-28, 1981, Vancouver, British Columbia, pp. 674-679.

(56) References Cited

OTHER PUBLICATIONS

Lueangwattana, C. et al., "A Comparative Study of Video Signals for Non-contact Heart Rate Measurement," 12th International Conference on Electiical Engineering/Electronics, Computer, Telecommunications and Information Technology (ECTI-CON), Jun. 24-27, 2015, Hua Hin, Cha-am, Thailand, IEEE, 5 pages.

Nisar, H. et al., "Chapter 5: A Simple Non-Invasive Automated Heart Rate Monitoring System Using Facial Images," Biomedical Image Analysis and Mining Techniques for Improved Health Outcomes, 2015, IGI Global, pp. 100-122.

Palus, H., "Representations of colour images in different colour spaces," The Colour Image Processing Handbook, 1998, Chapman & Hall, pp. 68-90.

Poh, M.-Z., et al., "Non-contact, automated cardiac pulse measurements using video imaging and blind source separation," Optics Express, vol. 18, No. 10, May 2010, Optical Society of America, pp. 10762-10774.

Raghuram, M., et al., "On the performance of wavelets in reducing motion artifacts from photoplethysmographic signals," IEEE 2010 4th International Conference on Bioinformatics and Biomedical Engineering (iCBBE), Jun. 18-20, 2010, Chengdu, China, IEEE, 4 pages.

Shao, D., et al., "Noncontact Monitoring of Blood Oxygen Saturation Using Camera and Dual-Wavelength Imaging System," IEEE Transactions on Biomedical Engineering, vol. 63, No. 6, Jun. 2016, IEEE, 8 pages.

Shao, D., et al., "Noncontact Monitoring Breathing Pattern, Exhalation Flow Rate and Pulse Transit Time," IEEE Transactions on Biomedical Engineering, vol. 61, No. 11, Nov. 2014, IEEE, pp. 2760-2767.

Shi, J. et al., "Good Features to Track," IEEE Conference on Computer Vision and Pattern Recognition (CVPR94), Jun. 1994, Seattle, WA, USA, IEEE, 8 pages.

Sinex, J.E., "Pulse oximetry: Principles and limitations," The American Journal of Emergency Medicine, vol. 17, No. 1, Jan. 1999, W.B. Saunders Company, pp. 59-66.

Sun, Y., et al., "Motion-compensated noncontact imaging photoplethysmography to monitor cardiorespiratory status during exercise," Journal of Biomedical Optics, vol. 16, No. 7, Jul. 2011, SPIE, pp. 077010-077010-9.

Sun, Y., et al., "Noncontact imaging photoplethysmography to effectively access pulse rate variability," Journal of Biomedical Optics, vol. 18, No. 6, Jun. 2013, SPIE, pp. 061205-061205.

Tkalcic, M. et al., "Colour spaces—perceptual, historical and applicational background," The IEEE Region 8 EUROCON 2003, Computer as a Tool, Sep. 2003, IEEE, 5 pages.

Tomasi, C. et al., "Shape and Motion from Image Streams: a Factorization Method—Part 3—Detection and Tracking of Point Features," Apr. 1991, School of Computer Science, Carnegie Mellon University, Pittsburgh, PA, 38 pages.

Tulyakov, S., et al., "Self-adaptive matrix completion for heart rate estimation from face videos under realistic conditions," Proceedings of the IEEE Conference on Computer Vision and Pattern Recognition, 2016, pp. 2396-2404.

Verkruysse, W. et al., "Remote plethysmographic imaging using ambient light," Optics Express, vol. 16, No. 26, Dec. 2008, Optical Society of America, pp. 21434-21445.

Viola, P. et al., "Rapid Object Detection using a Boosted Cascade of Simple Features," Proceedings of the 2001 IEEE Computer Society Conference on Computer Vision and Pattern Recognition (CVPR), 2001, IEEE, pp. I-511-I-518.

Wang, S.-J., et al., "Micro-Expression Recognition Using Color Spaces," IEEE Transactions on Image Processing, vol. 24, No. 12, Dec. 2015, IEEE, pp. 6034-6047.

Yam, K.L. et al., "A simple digital imaging method for measuring and analyzing color of food surfaces," Journal of Food Engineering, vol. 61, No. 1, 2004, Elsevier Ltd., pp. 137-142.

International Search Report and Written Opinion for International Patent Application No. PCT/US2017/052744, dated Nov. 16, 2017, 10 pages.

International Preliminary Report on Patentability for International Patent Application No. PCT/US2017/052744, dated Apr. 4, 2019, 9 pages.

U.S. Appl. No. 16/490,749.
U.S. Appl. No. 16/526,883.
U.S. Appl. No. 16/584,120.

* cited by examiner

| subject # | a* (ms) | g* (ms) | subject # | a* (ms) | g* (ms) |
|---|---|---|---|---|---|
| 1 | 30.7 | 54.4 | 10 | 56.1 | 83.2 |
| 2 | 44.0 | 207.7 | 11 | 40.2 | 98.0 |
| 3 | 42.2 | 97.0 | 12 | 45.3 | 72.0 |
| 4 | 47.5 | 145.5 | 13 | 67.3 | 122.9 |
| 5 | 67.2 | 146.7 | 14 | 30.5 | 50.4 |
| 6 | 40.7 | 66.8 | 15 | 36.8 | 123.3 |
| 7 | 21.2 | 80.5 | 16 | 29.9 | 55.5 |
| 8 | 44.7 | 81.9 | 17 | 24.3 | 84.6 |
| 9 | 34.9 | 60.1 | | | |

FIG. 12

SYSTEMS AND METHODS FOR COMPUTER MONITORING OF REMOTE PHOTOPLETHYSMOGRAPHY BASED ON CHROMATICITY IN A CONVERTED COLOR SPACE

RELATED APPLICATION

This application is a 35 U.S.C. 371 national phase filing of International Patent Application No. PCT/US2017/052744, filed Sep. 21, 2017, which claims the benefit of U.S. Provisional Patent Application No. 62/397,530, filed Sep. 21, 2016, the disclosures of which are hereby incorporated herein by reference in their entireties.

GOVERNMENT RIGHTS IN INVENTION

This invention was made with government support under U01 EB021980 awarded by the National Institutes of Health. The government has certain rights in the invention.

TECHNICAL FIELD

This disclosure relates to computer monitoring of remote photoplethysmography (rPPG) from camera images.

BACKGROUND

Photoplethysmography (PPG) is an essential tool to monitor patients' vital signs in medical practice. See Garbey, M., et al., *Contact-free measurement of cardiac pulse based on the analysis of thermal imagery*, IEEE Transactions on Biomedical Engineering, 2007, 54(8): p. 1418-1426; and Sinex, J. E., *Pulse oximetry: Principles and limitations*, The American Journal of Emergency Medicine, 1999, 17(1): p. 59-66, the disclosures of which are hereby incorporated herein by reference in their entirety. Traditional PPG requires contact with the skin, causing discomfort and even skin damage when used over a long period of time. See Sun, Y., et al., *Noncontact imaging photoplethysmography to effectively access pulse rate variability*, Journal of Biomedical Optics, 2012. 18(6): p. 061205, the disclosure of which is hereby incorporated herein by reference in its entirety. Recently, remote photoplethysmography (rPPG) has been proposed for contactless monitoring of a subject's PPG using a camera (e.g., video camera). See Litong, F., et al., *Dynamic ROI based on K-means for remote photoplethysmography*, 2015 IEEE International Conference on Acoustics, Speech and Signal Processing (ICASSP), 2015; Blackford, E. B. and J. R. Estepp, *Effects of frame rate and image resolution on pulse rate measured using multiple camera imaging photoplethysmography*, SPIE Medical Imaging, 2015, International Society for Optics and Photonics; Haque, M. A., et al., *Heartbeat Rate Measurement from Facial Video*, IEEE Intelligent Systems, 2015; Shao, D., et al., *Noncontact Monitoring of Blood Oxygen Saturation Using Camera and Dual-Wavelength Imaging System*, 2015; Shao, D., et al., *Noncontact Monitoring Breathing Pattern, Exhalation Flow Rate and Pulse Transit Time, IEEE Transactions on Biomedical Engineering*, 2014, 61(11): p. 2760-2767; and Clifton, D. A., M. C. V. Montoya, and L. Tarassenko, *Remote monitoring of vital signs*, 2012, Google Patents, the disclosures of which are hereby incorporated herein by reference in their entirety. rPPG is attractive because it can potentially track the subject's PPG under free-living conditions, while he/she is performing daily activities (e.g., working on a computer or watching television at home or in the workplace).

Most rPPG methods reported to date focus on still subjects in laboratory settings. In realistic settings (e.g., in hospitals or the patient's home), motion artifacts due to motion of the subject have been a challenge for reliable rPPG. See Sun, Y., et al., *Motion-compensated noncontact imaging photoplethysmography to monitor cardiorespiratory status during exercise*, Journal of Biomedical Optics, 2011, 16(7): p. 077010-077010-9; and Poh, M.-Z., D. J. McDuff, and R. W. Picard, *Non-contact, automated cardiac pulse measurements using video imaging and blind source separation*, Optics express, 2010, 18(10): p. 10762-10774, the disclosures of which are hereby incorporated herein by reference in their entirety. Many cameras capture images in RGB color space, which may provide a good signal for still subjects, but is susceptible to contamination by motion artifacts in realistic situations (e.g., subject movement).

Various methods have been developed to reduce motion-induced artifacts. See Shan, C., *Motion robust vital signal monitoring*, 2013, Google Patents; Yoo, S. K., *Photoplethysmography (PPG) device and the method thereof*, 2008, Google Patents; Lewandowska, M., J. Rumiński, and T. Kocejko, *Measuring pulse rate with a webcam—a non-contact method for evaluating cardiac activity*, Federated Conference on Computer Science and Information Systems (FedCSIS), 2011, IEEE; Vetter, R., et al., *Method and device for pulse rate detection*, 2006, Google Patents; Estepp, J. R., E. B. Blackford, and C. M. Meier, *Recovering pulse rate during motion artifact with a multi-imager array for non-contact imaging photoplethysmography*, 2014 IEEE International Conference on Systems, Man, and Cybernetics (SMC), 2014; and Tulyakov, S., et al., *Self-adaptive matrix completion for heart rate estimation from face videos under realistic conditions*, Proceedings of the IEEE Conference on Computer Vision and Pattern Recognition, 2016, the disclosures of which are hereby incorporated herein by reference in their entirety.

Independent component analysis (ICA) and principle component analysis (PCA) have been applied to separate the pulse signals of PPG from motion artifacts. See Poh, M.-Z., D. J. McDuff, and R. W. Picard, *Non-contact, automated cardiac pulse measurements using video imaging and blind source separation*, Optics express, 2010, 18(10): p. 10762-10774; Yoo, S. K., *Photoplethysmography (PPG) device and the method thereof*, 2008, Google Patents; Lewandowska, M., J. Rumiński, and T. Kocejko, *Measuring pulse rate with a webcam—a non-contact method for evaluating cardiac activity*, 2011 Federated Conference on Computer Science and Information Systems (FedCSIS), 2011, IEEE; and Vetter, R., et al., *Method and device for pulse rate detection*, 2006, Google Patents. These blind source separation algorithms often fail to recover rPPG signal from serious motion artifacts. See Feng, L., et al., *Motion artifacts suppression for remote imaging photoplethysmography*, 2014 19th International Conference on Digital Signal Processing (DSP), 2014, IEEE, the disclosure of which is hereby incorporated herein by reference in its entirety. Since rPPG signals have different amplitudes in the three channels of RGB color space, algorithms based on a combination of different color channels have been proposed to remove the motion artifacts. See Hulsbusch, M. and B. Rembold, *Ein bildgestütztes, funktionelles Verfahren zur optoelektronischen Erfassung der Hautperfusion*, 2008, RWTH Aachen Univ., Aachen, Germany, p. 70; Verkruysse, W., L. O. Svaasand, and J. S. Nelson, *Remote plethysmographic imaging using ambient light*, Optics express, 2008, 16(26): p. 21434-21445; and De Haan, G., *Device and method for extracting physiological information,* 2013, Google Patents, the disclosures of which are hereby incorporated herein by reference in their entirety. The essence of these methods is to analyze the motion artifacts in each channel, and then remove them via subtraction and normalization.

In summary, rPPG computer monitoring devices with a camera are attractive for non-invasive monitoring of a subject's physiological parameters, but rPPG computer monitoring devices are prone to motion-induced artifacts, making it difficult for such devices to obtain accurate readings in realistic situations.

Accordingly, there is a need for improved and more accurate rPPG computer monitoring devices, particularly rPPG computer monitoring devices that minimize the influence of motion-induced artifacts on monitoring of physiological parameters.

SUMMARY

Provided herein are systems and methods for computer monitoring of remote photoplethysmography (rPPG) from camera images based on chromaticity in a converted color space. See Tkalcic, M. and J. F. Tasic, *Colour spaces: perceptual, historical and applicational background,* Eurocon, 2003, the disclosure of which is hereby incorporated herein by reference in its entirety. Unlike RGB color space, CIELab color space is designed to approximate human vision, and separate illumination intensity changes (L* channel) from color changes (a* and b* channels). Motion artifacts mainly affect the illumination intensity (L* channel), so that CIELab color space can naturally isolate rPPG signals (a* and b* channels) from the motion artifacts. Accordingly, systems and methods disclosed herein employing a converted color space beneficially permit reduction of motion-induced artifacts in camera images for improved (rPPG) computer monitoring (e.g., measurements, tracking, readings, etc.) of physiological parameters. Although CIELab color space is disclosed, other non-RGB color spaces could be used. Additionally, various systems and methods disclosed herein include adaptive selection of a region of interest (ROI) and pruning of image frames by a computer system, such as when a face of a subject moves out of the view or is blocked by objects. In certain embodiments, a method automatically selects, by the computer system, an optimal ROI, removes frames in which the ROI is not clearly captured (e.g., moves out of the view or is blocked by the subject's hands), and analyzes rPPG in CIELab color space, rather than in RGB color space. Systems and methods disclosed herein may be used with subjects of varying and diverse skin tones, under realistic free-living conditions.

In one aspect, a remote photoplethysmography (rPPG) system for monitoring by a computer system of at least one physiological parameter of a living body from image data is disclosed. The rPPG system comprises a processor subsystem to electronically receive, at the computer system, a first image data set from an optical imaging element, the first image data set being representative of a series of consecutive images of at least a portion of the living body; convert, by the computer system, the first image data set from a first color space to a second color space to generate a second image data set including first channel data comprising a luminance component and second channel data comprising a chromatic component; and process, by the computer system, the second channel data to monitor the at least one physiological parameter of the living body.

In another aspect, a method for remote photoplethysmography (rPPG) monitoring by a computer system is disclosed. The method comprises electronically receiving, at the computer system, a first image data set from an optical imaging element, the first image data set being representative of a series of consecutive images of at least a portion of a living body; converting, by the computer system, the first image data set from a first color space to a second color space to generate a second image data set including first channel data comprising a luminance component and second channel data comprising a chromatic component; and processing, by the computer system, the second channel data to monitor at least one physiological parameter of the living body.

In another aspect, a non-transitory computer readable medium containing program instructions for execution by a processor of a computer system causes the computer system to perform the following steps: electronically receiving, at the computer system, a first image data set from an optical imaging element, the first image data set being representative of a series of consecutive images of at least a portion of a living body; converting, by the computer system, the first image data set from a first color space to a second color space to generate a second image data set including first channel data comprising a luminance component and second channel data comprising a chromatic component; and processing, by the computer system, the second channel data to monitor at least one physiological parameter of the living body.

In another aspect, a remote photoplethysmography (rPPG) system for monitoring by a computer system of at least one physiological parameter of a living body from image data is disclosed. The rPPG system being adapted to electronically receive, at the computer system, a first image data set from an optical imaging element, the first image data set being representative of a series of consecutive images of at least a portion of a living body; convert, by the computer system, the first image data set from a first color space to a second color space to generate a second image data set including first channel data comprising a luminance component and second channel data comprising a chromatic component; and process, by the computer system, the second channel data to monitor at least one physiological parameter of the living body.

In another aspect, a computer program comprising instructions which, when executed by at least one processor, causes the at least one processor to carry out electronically receiving, at the computer system, a first image data set from an optical imaging element, the first image data set being representative of a series of consecutive images of at least a portion of a living body; converting, by the computer system, the first image data set from a first color space to a second color space to generate a second image data set including first channel data comprising a luminance component and second channel data comprising a chromatic component; and processing, by the computer system, the second channel data to monitor at least one physiological parameter of the living body.

In another aspect, a computer program comprising instructions which, when executed by at least one processor, causes the at least one processor to carry out any of the above (and/or below). In certain embodiments, a carrier comprises the computer program above (and/or below), wherein the carrier is one of an electronic signal, an optical signal, a radio signal, or a computer readable storage medium.

In certain embodiments, the first color space comprises an RGB color space. In certain embodiments, the second color space comprises at least one of: a CIELab color space, wherein the first channel data comprises L* channel data, and the second channel data comprises at least one of a* channel data or b* channel data; or a YCbCr color space, wherein the first channel data comprises Y* channel data, and the second channel data comprises at least one of Cb* channel data or Cr* channel data. In certain embodiments, the at least one physiological parameter comprises at least one (or at least two, or all three) of breathing pattern, respiration rate, or heart rate.

In certain embodiments, the rPPG system, method, and/or non-transitory computer readable medium further comprise automatically determining, by the computer system, a region of interest (ROI) of the living body in the first image data set. In certain embodiments, the ROI is determined using a Viola-Jones face detection algorithm.

In certain embodiments, the rPPG system, method, and/or non-transitory computer readable medium further comprise tracking, by the computer system, the ROI through at least some consecutive images of the series of consecutive images. In certain embodiments, the ROI is tracked using a Kanade-Lucas-Tomasi algorithm. In certain embodiments, the rPPG system, method, and/or non-transitory computer readable medium further comprise initializing, by the computer system, the ROI based on a first image of the series of consecutive images, and reinitializing, by the computer system, the ROI after a predetermined number of images of the series of consecutive images. In certain embodiments, the rPPG system, method, and/or non-transitory computer readable medium further comprise removing, by the computer system, one or more consecutive images of the series of consecutive images if a number of identified feature points in the ROI in the one or more consecutive images is below a predetermined threshold. In certain embodiments, the predetermined threshold is 70%.

BRIEF DESCRIPTION OF THE DRAWINGS

FIG. 12 is a table showing errors in P-P intervals from a* channel and G* channel rPPG.

DETAILED DESCRIPTION

Figure 1A:
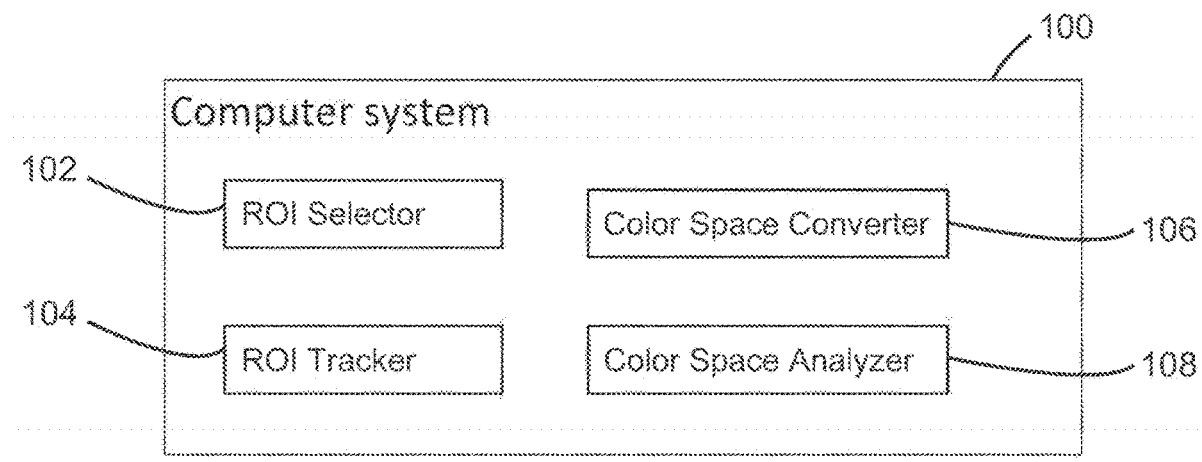
FIG. 1A is a schematic diagram of a computer system capable of monitoring remote photoplethysmography (rPPG) from camera images based on chromaticity in a converted color space according to the present disclosure.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below," "above," "upper," "lower," "horizontal," and/or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Provided herein are systems and methods for computer monitoring of remote photoplethysmography (rPPG) from camera images based on chromaticity in a converted color space. Unlike other color spaces, CIELab color space, for example, is designed to approximate human vision, and is designed to separate illumination intensity changes (channel L*) from color changes (channels a* and b*). Motion artifacts mainly affect the illumination intensity (channel L*), so that CIELab color space can naturally isolate rPPG signals (channels a* and b*) from the motion artifacts. Accordingly, systems and methods according to various embodiments disclosed herein reduce motion-induced artifacts in camera images for improved (rPPG) computer monitoring (e.g., measurements, tracking, readings, etc.) of physiological parameters. Although various embodiments disclosed herein are specifically directed to CIELab color space, upon review of the present disclosure, one skilled in the art will recognize that the present disclosure may be applied to other color spaces. Additionally, systems and methods according to at least certain embodiments include adaptive selection of region of interest (ROI) and pruning of image frames by a computer system, such as when the subject's face moves out of the view or is blocked by objects. The method automatically selects, by the computer system, an optimal ROI, removes frames in which the ROI is not clearly captured, and analyzes rPPG in CIELab color space, rather than in RGB color space. The systems and methods disclosed herein could be used with subjects of varying and diverse skin tones, under realistic free-living conditions.

The present disclosure relates to systems and methods (e.g., color space algorithm, color space-based algorithm, color space filter, etc.) capable of removing or minimizing subject motion-induced artifacts in electronic monitoring (e.g., measurements, tracking, readings, etc.) of physiological parameters (e.g., breathing pattern, respiration rate, heart rate, vital signs, etc.) by a computer system. In certain embodiments, a computer system can convert a first electronic monitoring signal in RGB color space to a second electronic monitoring signal in CIELab color space. The computer system achieves robust tracking of rPPG signal under realistic conditions, where the subject is allowed to move naturally.

Figure 1B:
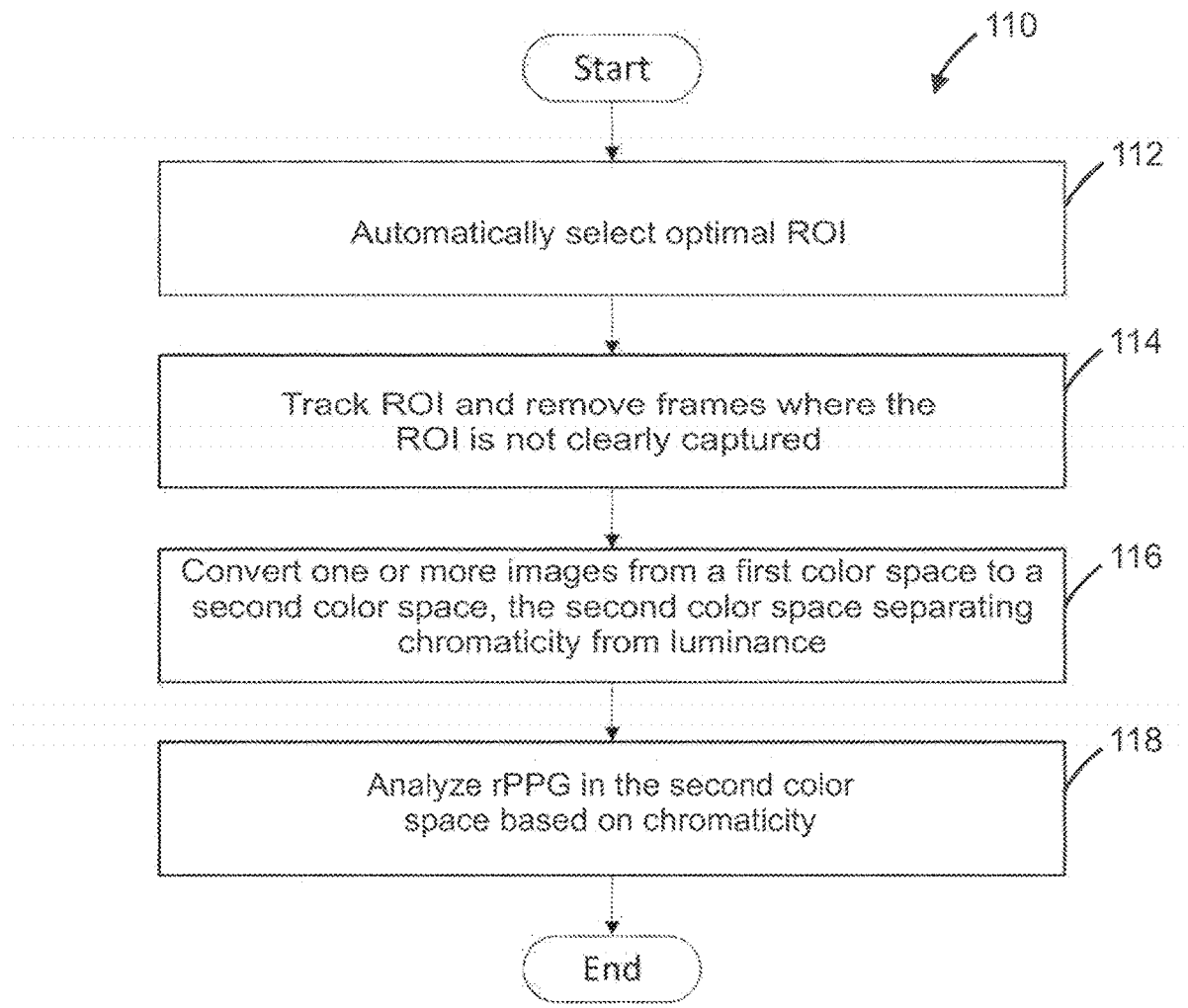
FIG. 1B is a flowchart illustrating steps carried out by the computer system of FIG. 1A for monitoring physiological parameters of a living body.

FIGS. 1A and 1B illustrate one embodiment of a computer system configured for monitoring remote photoplethysmography (rPPG) from camera images based on chromaticity in a converted color space according to the present disclosure. More specifically, FIG. 1A illustrates a computer system 100 with an ROI selector 102, an ROI tracker 104, a color space converter 106, and a color space analyzer 108, as explained in more detail below.

FIG. 1B illustrates processing steps of a method 110 carried out by the computer system 100 of FIG. 1A. As shown in FIG. 1B, in step 112, the computer system 100 automatically selects an optimal ROI (also referred to herein as ROI), such as by the ROI selector 102 of the computer system 100. In particular, in certain embodiments, the computer system 100 automatically identifies a subject's face, and then automatically selects the forehead and/or cheek areas as the optimal ROI. In step 114, the computer system 100 then tracks the ROI and removes frames when the ROI is not clearly captured (e.g., when the ROI moves out of the view or is blocked by the subject's hands), such as by the ROI tracker 104 of the computer system 100. In realistic situations (e.g., a subject working on a computer), the subject is not static, and his/her body motions may corrupt an rPPG signal. To minimize the influence of motion-induced artifacts on computer measurements, the computer system 100 first determines an optimal ROI for rPPG signal extraction, and then tracks the ROI. See Tomasi, C. and T. Kanade, *Detection and tracking of point features*, 1991: School of Computer Science, Carnegie Mellon Univ., Pittsburgh, the disclosure of which is hereby incorporated herein by reference in its entirety. The subject may move frequently, for example: turning his/her head, raising his/her hands, and/or standing up. In such events, the ROI might be blocked by hands or move out of the image frame. The computer system 100 detects such events, and removes the corresponding image frames.

In step 116, the computer system 100 then converts one or more images from a first color space (e.g., RGB color space) to a second color space (e.g., CIELab color space) separating chromaticity from luminance, such as by the color space converter 106 of the computer system 100. For example, the computer system 100 determines rPPG signal in CIELab color space. L* channel (also referred to herein as *L channel) is most prone to motion-induced artifacts because the motion usually affects the intensity distribution more than the color. b* channel (also referred to herein as *b channel) provides better rPPG than L*, but a* channel (also referred to herein as *a channel) appears to provide even more robust rPPG. In certain embodiments, the computer system 100 could be implemented in a home care unit, installed onto a computing device (e.g., desktop computer, laptop, tablet, smartphone, etc.) with an external or internal camera, or implemented on a computing device with electronic access (e.g., over the Internet) to image data (e.g., video data, photo data, etc.). In step 118, the computer system 100 analyzes rPPG in the second color space (e.g., CIELab color space rather than in RGB color space) based on chromaticity, such as by the color space analyzer 108 of the computer system 100. The computer system 100 can be combined with other signal de-noising methods (e.g., a wavelet de-noising method and/or an adaptive filter) to further improve performance. See Raghuram, M., et al., *On the Performance of Wavelets in Reducing Motion Artifacts from Photoplethysmographic Signals*, 2010 4th International Conference on Bioinformatics and Biomedical Engineering (iCBBE), 2010; and Feng, L., et al., *Motion-Resistant Remote Imaging Photoplethysmography Based on the Optical Properties of Skin*, IEEE Transactions on Circuits and Systems for Video Technology, 2015, 25(5), the disclosures of which are hereby incorporated herein by reference in their entirety. System accuracy was validated from findings of a pilot study, including 17 subjects under ambient conditions (e.g., illuminated with a fluorescent lamp). The results were compared with the RGB color space analysis, and the performance was evaluated using heart rate correlation with the ECG (electrocardiogram), signal-to-noise ratio, and error of peak-to-peak interval.

Figure 2A:
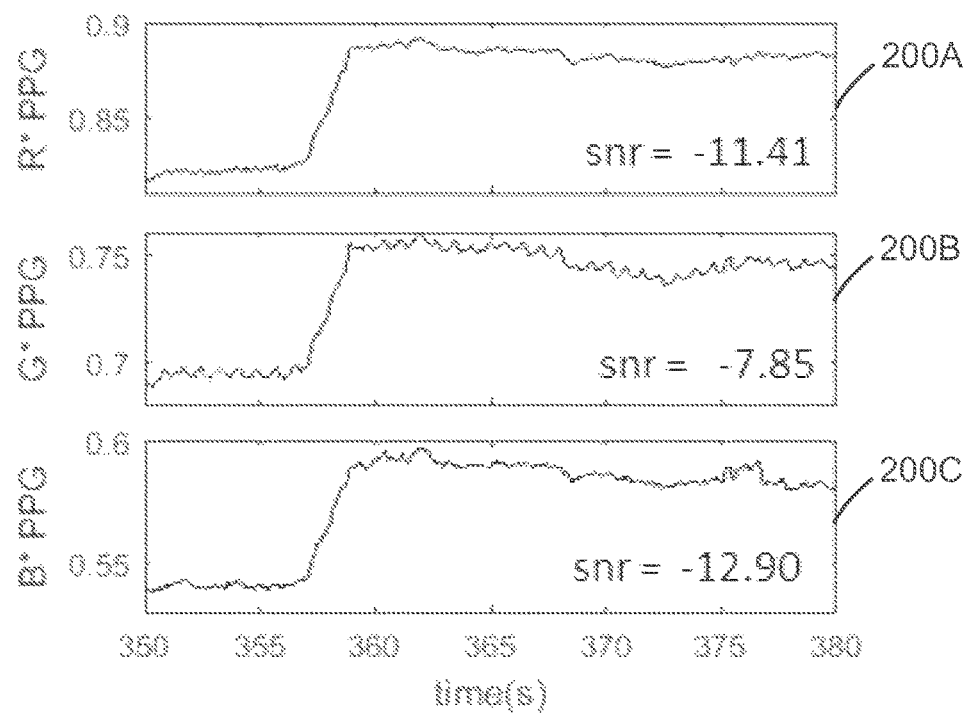
FIG. 2A includes three frames providing line charts of time-varying rPPG extraction signals for R*, G*, and B* channels corresponding to RGB color space for images obtained during a specified time period, with a superimposed signal-to-noise ratio (SNR) value for each channel.

FIGS. 2A-2D illustrate rPPG extraction from various color spaces, along with the signal-to-noise ratios for comparison of signal performance in the various color spaces. FIG. 2A includes three frames providing line charts of time-varying rPPG extraction signals for R*, G*, and B* channels corresponding to RGB color space for images obtained during a specified time period, with a superimposed SNR value for each channel. In particular, frame 200A corresponds to the R* channel, frame 200B corresponds to the G* channel (also referred to herein as g* channel), and frame 200C corresponds to the B* channel.

Figure 2B:
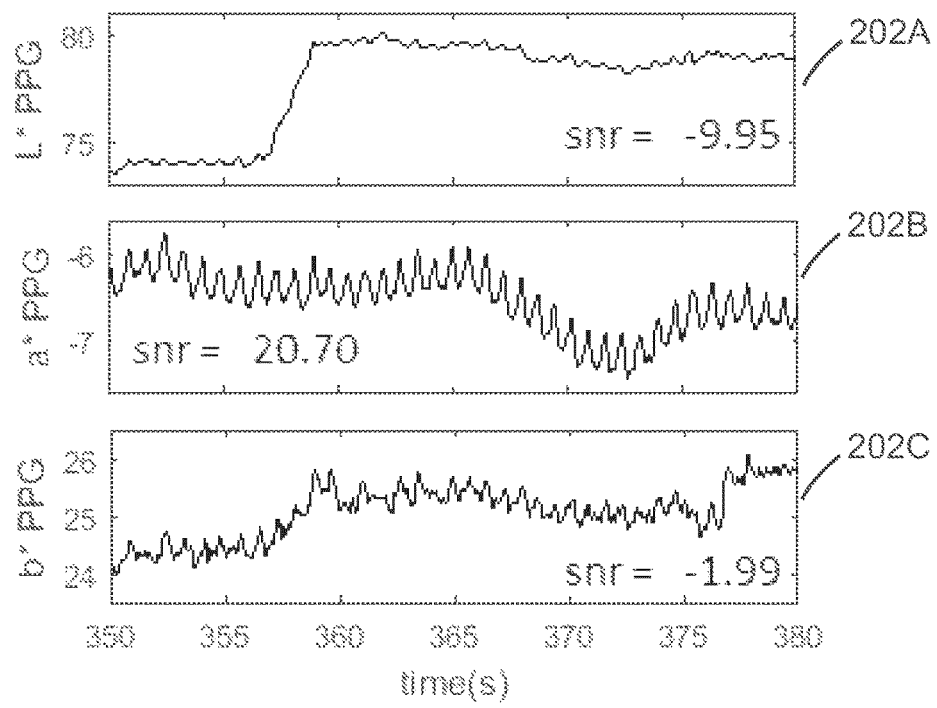
FIG. 2B includes three frames providing line charts of time-varying rPPG extraction signals for L*, a*, and b* channels corresponding to CIELab color space derived from image data represented in the charts of FIG. 2A, with a superimposed SNR value for each channel.

FIG. 2B includes three frames providing line charts of time-varying rPPG extraction signals for L*, a*, and b* channels corresponding to CIELab color space derived from image data represented in the charts of FIG. 2A, with a superimposed SNR value for each channel. In particular, frame 202A corresponds to the L* channel, frame 202B corresponds to the a* channel, and frame 202C corresponds to the b* channel.

Figure 2C:
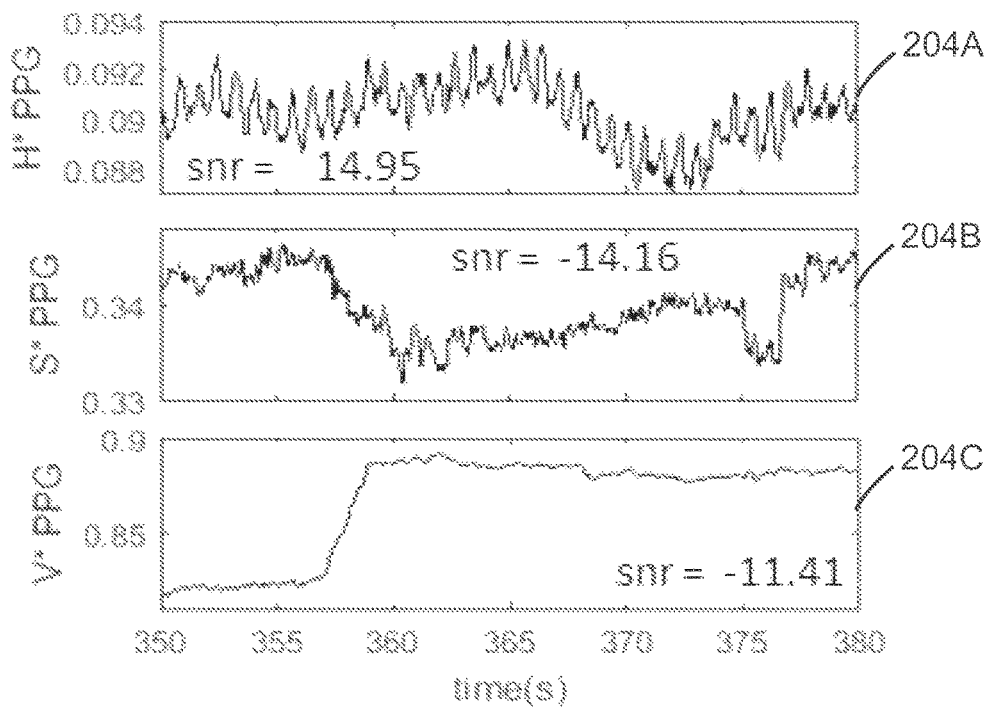
FIG. 2C includes three frames providing line charts of time-varying rPPG extraction signals for H*, S*, and V* channels corresponding to HSV color space, derived from image data represented in the charts of FIG. 2A, with a superimposed SNR value for each channel.

FIG. 2C includes three frames providing line charts of time-varying rPPG extraction signals for H*, S*, and V* channels corresponding to HSV color space, derived from image data represented in the charts of FIG. 2A, with a superimposed SNR value for each channel. In particular, frame 204A corresponds to the H* channel, frame 204B corresponds to the S* channel, and frame 204C corresponds to the V* channel.

Figure 2D:
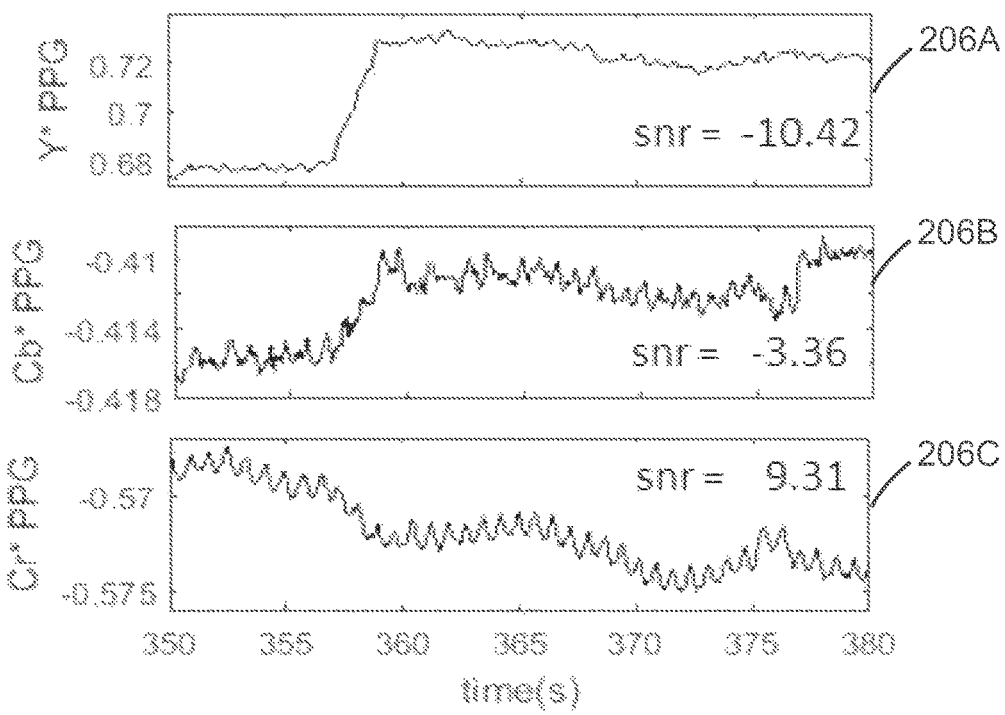
FIG. 2D includes three frames providing line charts of time-varying rPPG extraction signals for Y*, Cb*, and Cr* channels corresponding to YCbCr color space, derived from image data represented in the charts of FIG. 2A, with a superimposed SNR value for each channel.

FIG. 2D includes three frames providing line charts of time-varying rPPG extraction signals for Y*, Cb*, and Cr* channels corresponding to YCbCr color space, derived from image data represented in the charts of FIG. 2A, with a superimposed SNR value for each channel. In particular, frame 206A corresponds to the Y* channel, frame 206B corresponds to the Cb* channel, and frame 206C corresponds to the Cr* channel.

As pulsatile blood under the skin changes the skin-tone, while motion does not, a system and method according to one embodiment of the present disclosure convert a first color space to a second color space to separate motion represented in the intensity channel data from color changes in the chromaticity channel data. The results indicate that the chromaticity channels (e.g., a*, H*, and Cr*) from each color space provide better performance (e.g., better and cleaner signals) than the other channels, and channel a* from CIELab provides the best performance. Accordingly, systems and methods according to various embodiments of the present disclosure separate a signal into at least a chromaticity component and a luminance component (e.g., brightness component, lightness component, intensity component), and process the chromaticity component for rPPG computer monitoring of physiological parameters.

Figure 3A:
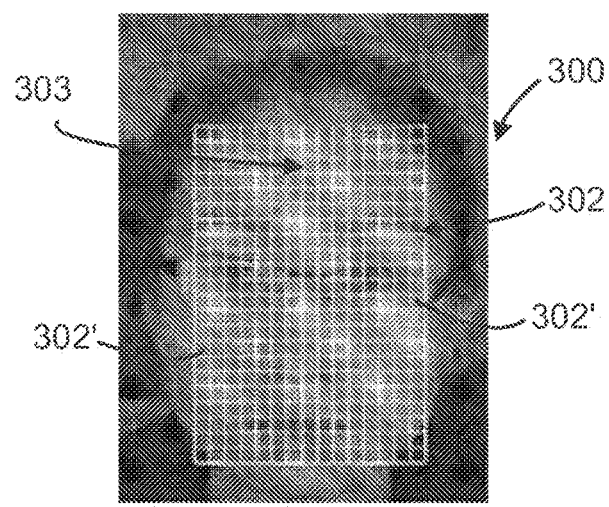
FIG. 3A shows a face area and division of the face area into three hundred and thirty (22×15) sub-areas.
Figure 3B:
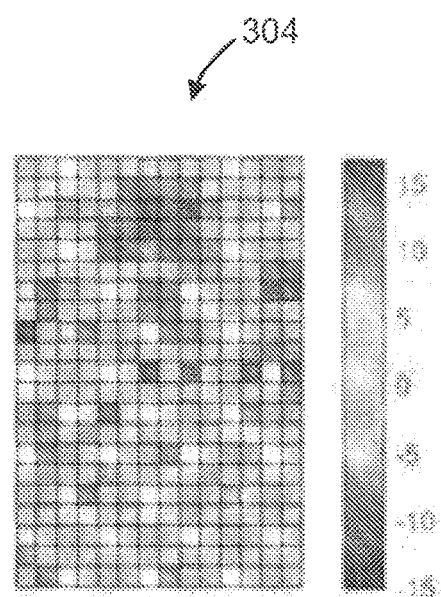
FIG. 3B is a signal-to-noise ratio (SNR) map corresponding to the sub-areas shown in FIG. 3A.

FIGS. 3A-3E illustrate ROI detection and tracking. The face 300 of the subject is first detected by a computer system (e.g., computer system 100 shown in FIG. 1A) with the Viola-Jones (VJ) face detection algorithm as illustrated by the rectangle bordering the grid in FIG. 3A, with such rectangle defining a face area 302. FIG. 3A shows division of the face area 302 into three hundred and thirty sub-areas 302' (calculated from the 22×15 grid). The VJ face detection algorithm based on Harr features can identify a multi-scaled face by training a boosted cascade of classifiers. See Viola, P. and M. Jones, *Rapid object detection using a boosted cascade of simple features*, Proceedings of the 2001 IEEE Computer Society Conference on Computer Vision and Pattern Recognition, 2001, *CVPR* 2001, IEEE, the disclosure of which is hereby incorporated herein by reference in its entirety.

The computer system divides the face area 302 into the three hundred and thirty sub-areas 302', with each sub-area 302' containing four hundred (20×20) pixels. The computer system then determines the signal-to-noise ratio (SNR) of the rPPG signal in each sub-area 302' as shown in a SNR map 304 in FIG. 3B, which corresponds to the sub-areas 302' shown in FIG. 3A. Also, for clarity, FIG. 3D provides a numerical SNR map 304' of the SNR map 304 of FIG. 3B.

Figure 3C:
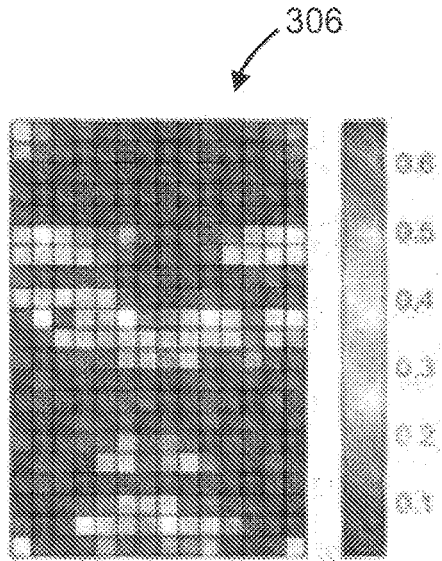
FIG. 3C is a roughness map corresponding to the sub-areas shown in FIG. 3A.
Figure 3D:
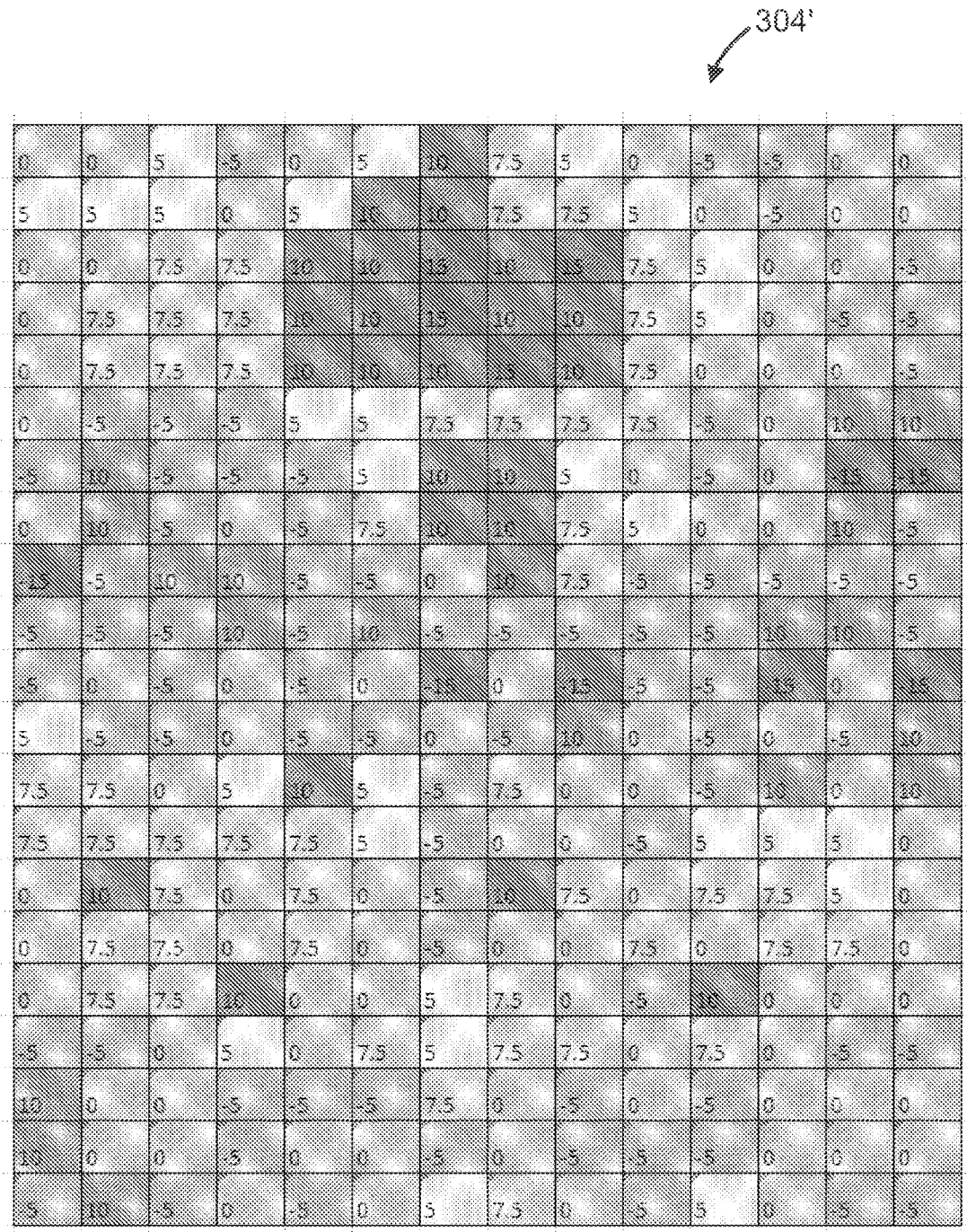
FIG. 3D provides a numerical SNR map of the SNR map of FIG. 3B.
Figure 3E:
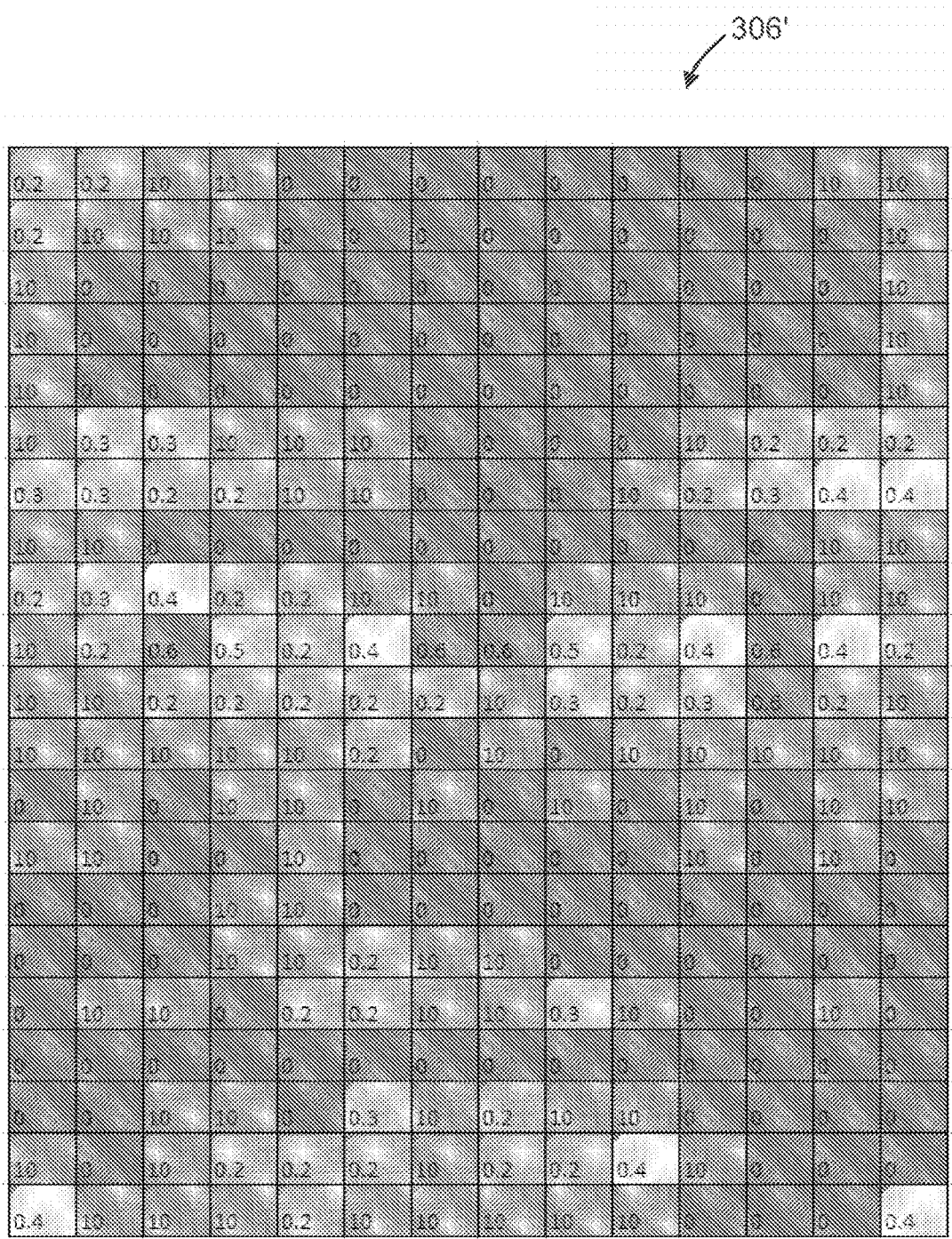
FIG. 3E provides a numerical SNR map of the roughness map of FIG. 3C.

As shown in the roughness map 306 of FIG. 3C (which corresponds to the sub-areas 302' shown in FIG. 3A), the most uniform areas are on the forehead and cheek areas. Also, for clarity, FIG. 3E provides a numerical SNR map 306' of the roughness map 306 of FIG. 3C. In this embodiment, the computer system (e.g., computer system 100 shown in FIG. 1A) automatically selects a region of ninety-six hundred (120×80) pixels from the most uniform area on the forehead as the optimal ROI 303 for rPPG (shown in FIG. 3A). This size could be empirically decided, such as according to experiment conditions (e.g., distance to camera) to ensure that a large enough feature area (such as forehead) is included.

In certain embodiments, in selecting the optimal ROI 303 the computer system focuses on the forehead and/or cheek areas, as the forehead provides some of the highest quality rPPG signals, followed by the cheek areas. See Gupta, O., D. McDuff, and R. Raskar, *Real-Time Physiological Measurement and Visualization Using a Synchronized Multi-Camera System*, Proceedings of the IEEE Conference on Computer Vision and Pattern Recognition Workshops, 2016, the disclosure of which is hereby incorporated herein by reference in its entirety. Also, in certain embodiments, the computer system selects the forehead as the optimal ROI 303 for rPPG because the forehead area minimizes complications due to facial expression changes, such as talking and smiling. Furthermore, as mentioned above, in selecting the optimal ROI 303, the computer system identifies the most uniform area on the forehead, which helps minimize light distribution changes on the face due to motion. The uniformity of an area is evaluated with the following formula ("Eq. 1"):

$$r = \frac{std(I(i, j))}{mean(I(i, j))}, \quad (1)$$

where I(i,j) is the intensity at pixel (i,j), std(I(i,j)) is standard deviation and mean(I(i,j)) is the mean intensity of the ROI. Since r in Eq. 1 measures the roughness of an area, a reduction in the value of r corresponds to increased uniformity of the area.

As the subject moves, the optimal ROI 303 is subject to change. To determine rPPG with the same optimal ROI 303, the computer system tracks the optimal ROI 303 with a tracking algorithm, such as with the Kanade-Lucas-Tomasi (KLT) algorithm. See Tomasi, C. and T. Kanade, *Detection and tracking of point features*, 1991: School of Computer Science, Carnegie Mellon Univ., Pittsburgh. Some of the motions could be large (e.g., sudden turning of head or waving hands in front of the face), which could cause the tracking algorithm to fail. To mitigate this problem, the corresponding image frames are pruned with the algorithm described below. The computer system calculates a motion vector that describes the motion-induced changes in the optimal ROI 303 by tracking feature points within the optimal ROI 303 with the KLT algorithm. See Id; and Lucas, B. D. and T. Kanade, *An iterative image registration technique with an application to stereo vision*, IJCAI, 1981, the disclosure of which is hereby incorporated herein by reference in its entirety. Using the motion vector, the computer system adjusts the location, shape, and size of the optimal ROI 303 for each frame. The computer system detects feature points within the optimal ROI 303 in the first frame using the corner point detection algorithm developed by Shi and Tomasi, and these feature points are then tracked on a frame-by-frame basis. See Jianbo, S. and C. Tomasi, *Good features to track*, 1994 IEEE Computer Society Conference on Computer Vision and Pattern Recognition, 1994, the disclosure of which is hereby incorporated herein by reference in its entirety. Thresholding in the calculation causes loss of some points during tracking. See Viola, P. and M. Jones, *Rapid object detection using a boosted cascade of simple features*, Proceedings of the 2001 IEEE Computer Society Conference on Computer Vision and Pattern Recognition, 2001, CVPR 2001, IEEE. To minimize errors arising from the loss of points, the computer system reinitializes the feature points for every 900 frames (corresponding to 30 s). When a large motion occurs, many of the feature points are lost. If too many feature points are lost, then tracking of the optimal ROI 303 becomes difficult or meaningless. The computer system prunes image frames in which over 30% of the feature points are lost.

CIELab color space is perceptually uniform (e.g., the Euclidean distance between two different colors corresponds approximately to the color difference perceived by the human eye). See Tkalcic, M. and J. F. Tasic, *Colour spaces: perceptual, historical and applicational background*, Eurocon, 2003, the disclosure of which is hereby incorporated herein by reference in its entirety. Channel L* is the luminance or lightness component, which ranges from 0 to 100. Channels a* and b* are two chromatic components, both ranging from −120 to 120. See Yam, K. L. and S. E. Papadakis, *A simple digital imaging method for measuring and analyzing color of food surfaces*, Journal of Food Engineering, 2004, 61(1): p. 137-142, the disclosure of which is hereby incorporated herein by reference in its entirety. To convert an image in RGB to CIELab color space, the computer system first converts the image into XYZ color space, as shown below, $$\begin{bmatrix} X \\ Y \\ Z \end{bmatrix} = \begin{bmatrix} 0.431 & 0.342 & 0.178 \\ 0.222 & 0.707 & 0.071 \\ 0.020 & 0.130 & 0.939 \end{bmatrix} \begin{bmatrix} R_{norm} \\ G_{norm} \\ B_{norm} \end{bmatrix} \quad (2)$$

where $R_{norm}$, $G_{norm}$, and $B_{norm}$ denote the three channels after normalization by (R+G+B). See Wang, S.-J., et al., *Micro-Expression Recognition Using Color Spaces*, IEEE Transactions on Image Processing, 2015, 24(12): p. 6034-6047, the disclosure of which is hereby incorporated herein by reference in its entirety. The normalization helps reduce the illumination non-uniformity. The channels of CIELab can be calculated as, $$L^* = \begin{cases} 116 \times \left(\frac{Y}{Y_n}\right)^{\frac{1}{3}} - 16, & \frac{Y}{Y_n} > 0.008856 \\ 903 \times \left(\frac{Y}{Y_n}\right), & \frac{Y}{Y_n} \leq 0.008856 \end{cases} \quad (3)$$

$$a^* = 500 \times \left(f\left(\frac{X}{X_n}\right) - f\left(\frac{Y}{Y_n}\right)\right) \quad (4)$$

$$b^* = 200 \times \left(f\left(\frac{Y}{Y_n}\right) - f\left(\frac{Z}{Z_n}\right)\right) \quad (5)$$

where $X_n$, $Y_n$, and $Z_n$ are the CIE XYZ tristimulus values of the reference white point, and $$f(t) = \begin{cases} t^{\frac{1}{3}}, & t > 0.008856 \\ 7.787 \times t + \frac{16}{116}, & t \leq 0.008856 \end{cases} \quad (6)$$

While the green (G*) channel in RGB color space may be used for rPPG tracking, RGB color space is device-dependent, non-intuitive, and perceptually non-uniform, and its three components are highly correlative with cross correlation coefficients of ~0.78 (between B* and R* channels), ~0.98 (between R* and G*) and ~0.94 (between G* and B*). See Tkalcic, M. and J. F. Tasic, *Colour spaces: perceptual, historical and applicational background*, in Eurocon. 2003; and Palus, H., *Representations of colour images in different colour spaces*, The Colour image processing handbook, 1998, Springer, p. 67-90, the disclosures of which are hereby incorporated herein by reference in their entirety. In contrast, CIELab color space separates the intensity and chromaticity components. CIELab is superior for robust rPPG because the motion of the subject mainly changes the intensity, and PPG arising from heart beats changes both the intensity and chromaticity of the skin.

Figures 4A, 4B, 4C:
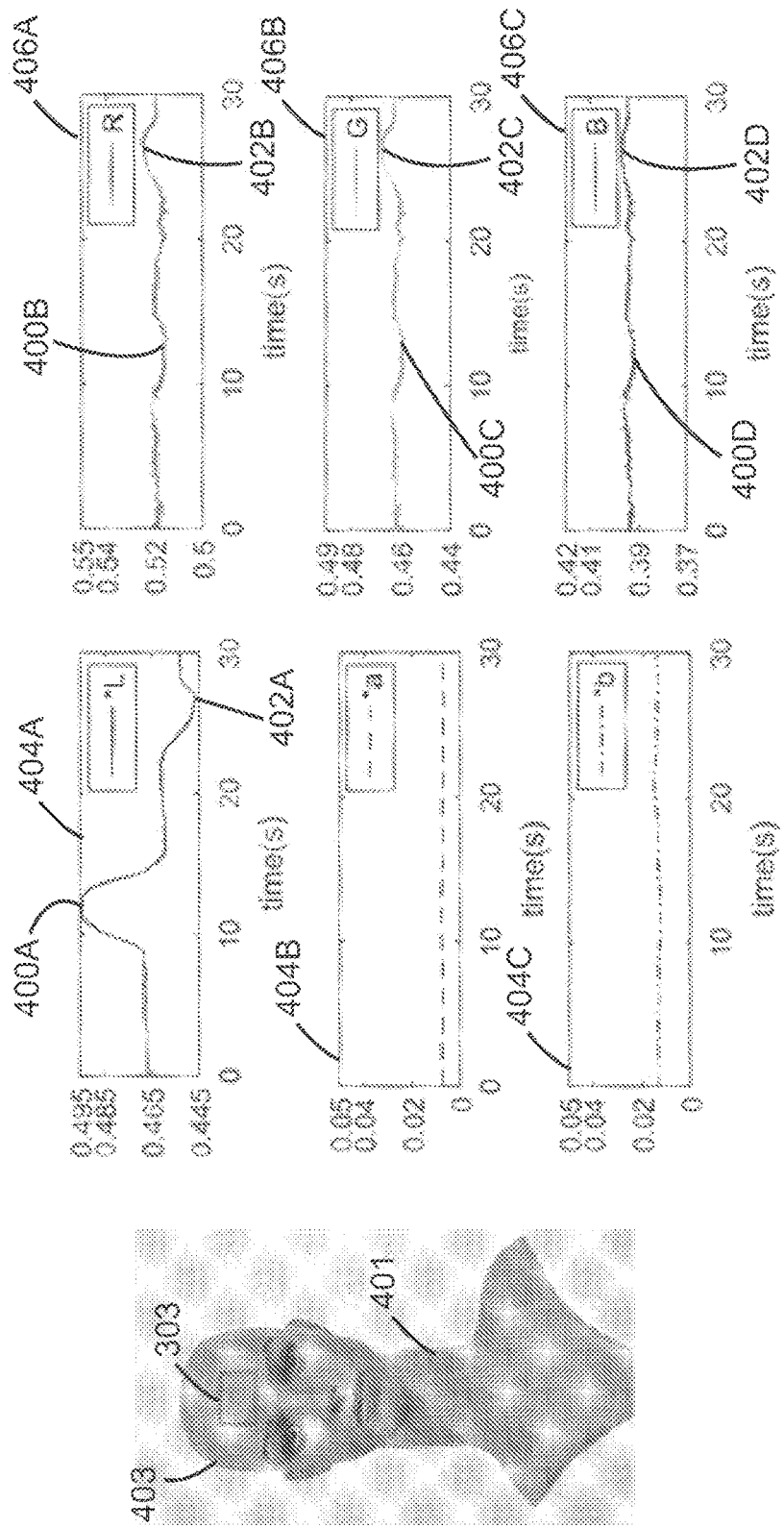
FIG. 4A shows a region of interest (ROI) selection on the forehead of a mannequin.
FIG. 4B includes three frames providing line charts of time-varying signals for L*, a*, and b* channels corresponding to CIELab color space obtained during a specified time period, with the uppermost frame in particular showing motion-induced changes apparent in the L* channel line chart.
FIG. 4C includes three frames providing line charts of time-varying signals for R*, G*, and B* channels corresponding to RGB color space obtained during the same time period of FIG. 4B, with each frame showing motion-induced changes (i.e., in each of the in R*, G*, and B* channels)

FIGS. 4A-4C illustrate motion artifacts obtained using a mannequin 401 subject to manually induced motion. FIG. 4A shows a region of interest (ROI) selection on the forehead of the mannequin 401. More specifically, as shown in FIG. 4A, an optimal ROI 303 was selected (by the user and/or automatically by a computer system (e.g., computer system 100 shown in FIG. 1A)) on the forehead 403 of the mannequin 401 and tracked with the KLT algorithm.

FIG. 4B includes three frames providing line charts of time-varying signals for L*, a*, and b* channels corresponding to CIELab color space obtained during a specified time period, with the uppermost frame in particular showing motion-induced changes apparent in the L* channel line chart. The changes in the three channels were normalized for comparison. In particular, frame 404A corresponds to the L* channel, frame 404B corresponds to the a* channel, and frame 404C corresponds to the b* channel. Large variations (e.g., first variation 400A and second variation 402A) in the intensity channel L* (corresponding to frame 404A), occurred at 10-15 s and 25-30 s, which were due to motions of the mannequin 401. However, the chromaticity channels a* and b* (corresponding to frames 404B, 404C, respectively), showed little variation associated with the motions. Thus, the chromaticity channels a* and b* are more tolerant (e.g., less sensitive) to motion artifacts than the intensity channel L*. The chromaticity channels a* and b* are also more tolerant to the motion artifacts than R*, G*, B* channels that contain both intensity and chromaticity information as shown in FIG. 4C, which includes three frames providing line charts of time-varying signals for R*, G*, and B* channels corresponding to RGB color space obtained during the same time period as that of FIG. 4B, with each frame showing motion-induced changes. In particular, frame 406A corresponds to the R* channel, frame 406B corresponds to the G* channel, and frame 406C corresponds to the B* channel. Further, the R* channel (corresponding to frame 406A) shows a first variation 400B and a second variation 402B, the G* channel (corresponding to frame 406B) shows a first variation 400C and a second variation 402C, and the B* channel (corresponding to frame 406C) shows a first variation 400D and a second variation 402D. The first variations 400B, 400C, 400D and the second variations 402B, 402C, 402D correspond to motion of the mannequin 401 as in the *L channel.

Figure 5:
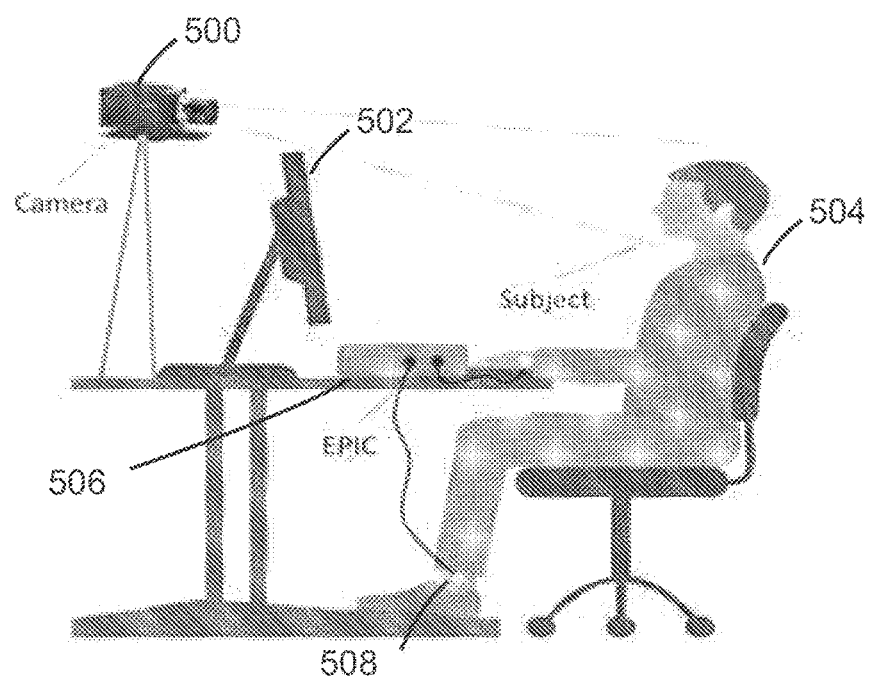
FIG. 5 is a schematic diagram showing an experimental setup for performing rPPG in a converted color space.

The effectiveness of the algorithm executed by the computer system 100 described above was examined in a pilot study including 17 subjects. The subjects consisted of 11 males and 6 females, with different ages (27.9±2.8 years), ethnic profiles (4 Caucasians, 9 Asians, and 4 with dark skin), and skin tones (light and dark colors). During the experiment, each subject was asked to sit and work on a computer naturally. FIG. 5 is a schematic diagram showing an experimental setup for performing rPPG in a converted color space. As shown in FIG. 5, a camera 500 (e.g., a Pike color camera (F-032C), although any color video camera could be used) was positioned behind a computer 502 at about 0.8 m from each subject 504. The camera 500 recorded a 10-minute video for each subject 504 under ambient light (e.g., with a regular fluorescent lamp), and the video was divided into 60 segments, each of 10 s duration. rPPG signal within a window of 20 s (two segments) was analyzed by the computer system, and the window was moved from the beginning to the end of the entire 10-minute video with a step of 10 s. The video recording frame rate was set to be 30 frames per second (f/s), and each frame contained 307.2K (480*640) pixels. During video recording, an ECG of the subject 504 was synchronously recorded with an ECG device 506 or Electric Potential Integrated Circuit (EPIC) (Plessey Semiconductors, Inc.), using a pair of electrodes 508 attached to the left wrist and ankle of the subject 504, respectively. Any suitable ECG device 506 could be used, and the ECG device 506 was provided only for comparison purposes with the accuracy of the system disclosed herein.

Figure 6A:
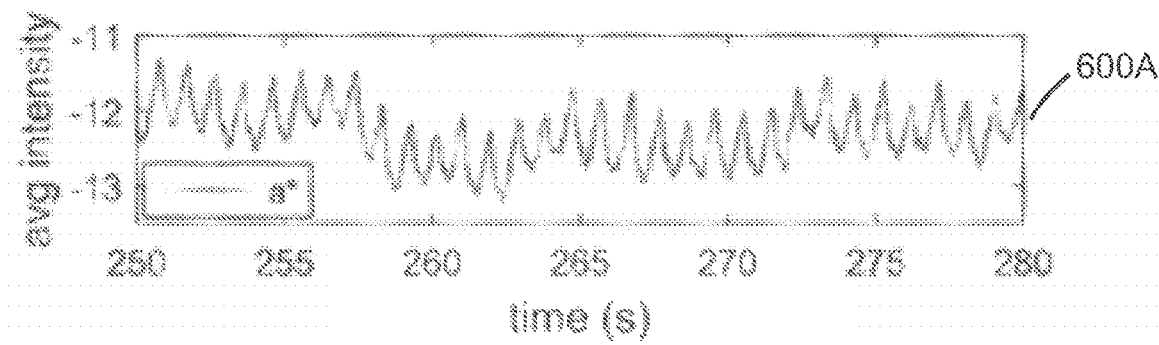
FIG. 6A is a line chart showing average intensity versus time (s) for an rPPG signal from channel a*.
Figure 6B:
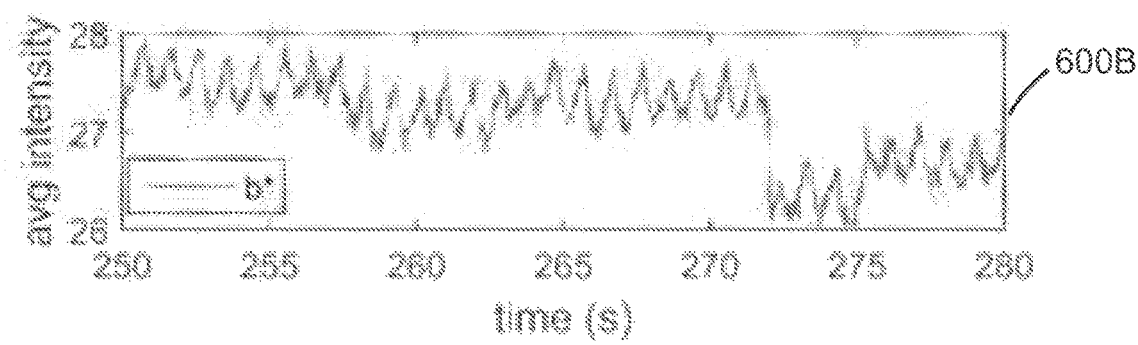
FIG. 6B is a line chart showing average intensity versus time (s) for an rPPG signal from channel b*.
Figure 6C:
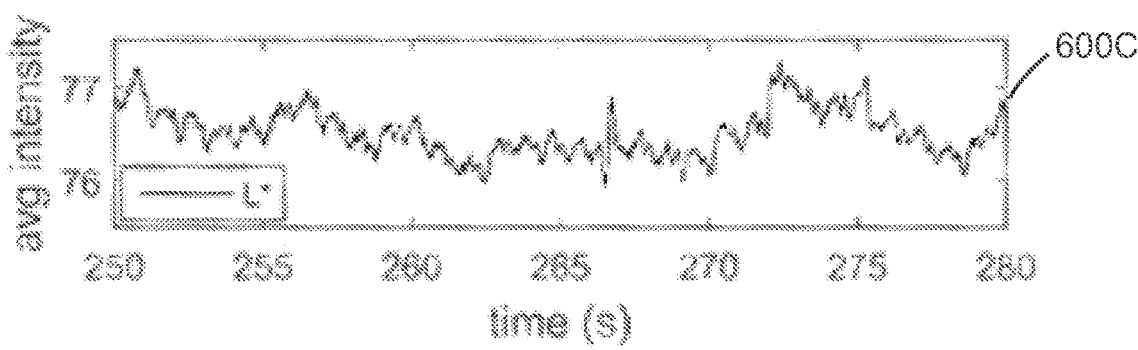
FIG. 6C is a line chart showing average intensity versus time (s) for an rPPG signal from channel L*.

Following the process described above, rPPG signals were extracted from the recorded videos for the different subjects. FIGS. 6A-6C illustrate examples of rPPG in a*, b*, and L* channels of CIELab color space. In particular, FIG. 6A is a line chart 600A showing average intensity versus time (s) for an rPPG signal from channel a*, FIG. 6B is a line chart 600B showing average intensity versus time (s) for an rPPG signal from channel b*, and FIG. 6C is a line chart 600C showing average intensity versus time (s) for an rPPG signal from channel L*. As shown, the rPPG signal is the cleanest in a* channel (shown in chart 600A) and most noisy in L* channel (shown in chart 600C), as the L* channel is the most sensitive to the motion artifacts. The rPPG in b* channel (shown in chart 600B) is better than that in L* channel, but not as clean as the rPPG in a* channel. Although both a* and b* channels are chromatic channels, a* channel performs better than b* channel for rPPG extraction. Blue spectral content in b* channel has less skin penetration, which may affect its sensitivity for rPPG sensing. See Bashkatov, A. N., et al., *Optical properties of human skin, subcutaneous and mucous tissues in the wavelength range from 400 to 2000 nm*, Journal of Physics D: Applied Physics, 2005, 38(15): p. 2543, the disclosure of which is hereby incorporated herein by reference in its entirety. Applicant recognizes that b* channel also contains yellow, which can penetrate deeper than blue, but not as deep as red in a* channel. Also, a RGB color camera cannot directly sense yellow, and therefore represents yellow with a combination of red and green. See *Allied Vsion*, available from: http://psirep.com/products/avt-pike-f-032-bc-fast-vga-camera-high-quality-1394b-firewire-208-fps#specifications&details, the disclosures of which are hereby incorporated herein by reference in their entirety. For these reasons, a* channel is better than b* channel for optimal rPPG detection.

Figure 7A:
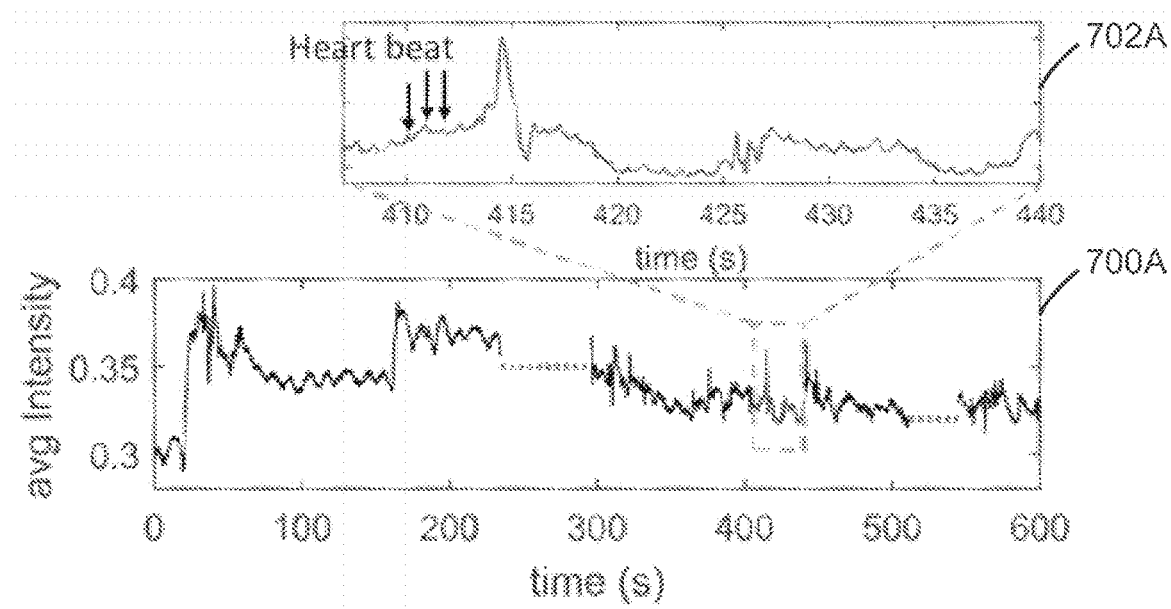
FIG. 7A is a line chart plotting an rPPG signal (average intensity versus time for a period of 0 to 600 seconds) of a living body in channel G* of RGB color space, with an upper inset line chart embodying a magnified portion of the rPPG signal for a time period of about 405 seconds to 440 seconds.
Figure 7B:
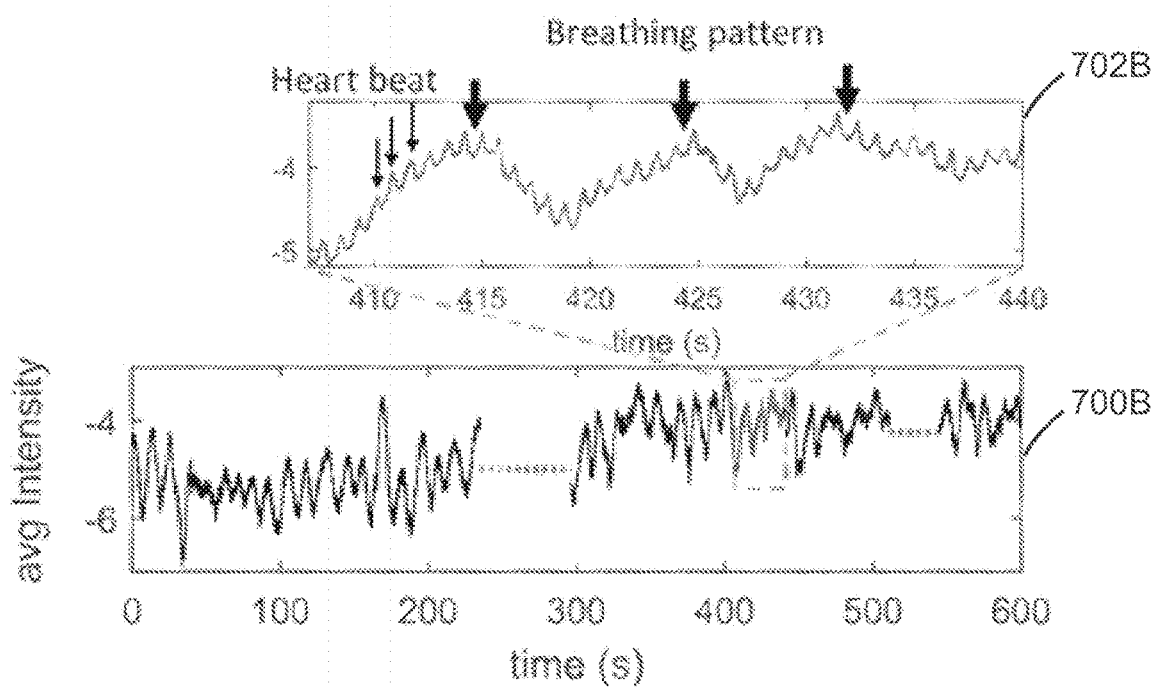
FIG. 7B is a line chart embodying a comparative plot of rPPG signals (average intensity versus time for the same period of 0 to 600 seconds) of the same living body as depicted in FIG. 7A, but in channel a* of CIELab color space, with an upper inset line chart embodying a magnified portion of the rPPG signal for the time period of about 405 seconds to 440 seconds.

In the RGB color space, G* channel generally provides the best rPPG, and as a result, was compared with a* channel. FIGS. 7A and 7B embody line charts plotting the rPPG signals extracted from a* channel and G* channel, respectively, of the same video. In particular, chart 700A in FIG. 7A corresponds to G* channel, and chart 700B in FIG. 7B corresponds to a* channel. Note that some sections of the video were pruned as described above and as illustrated in dashed lines in FIGS. 7A and 7B. FIG. 7A is a plot of rPPG signal (average intensity versus time for a period of 0 to 600 seconds) of a living body in channel G* of RGB color space, with an upper inset plot 702A embodying a magnified portion of the rPPG signal for a time period of about 405 seconds to 440 seconds. FIG. 7B is a comparative plot of rPPG signals (average intensity versus time for the same period of 0 to 600 seconds) of the same living body as depicted in FIG. 7A, but in channel a* of CIELab color space, with an upper inset plot 702B embodying a magnified portion of the rPPG signal for the time period of about 405 seconds to 440 seconds. Compared with G* rPPG in RGB color space (FIG. 7A), a* rPPG in CIELab color space (FIG. 7B) shows more clearly the breathing pattern with an average time interval of ~10 s. Close inspection of the rPPG signals in G* and a* at the same time interval reveals the heart beat signals, and the heart beat signal in a* (illustrated in the upper inset plot 702B) is far cleaner than that in G* (illustrated in the upper inset plot 702A). The large fluctuations in G* rPPG was due to head movements of the subject. The same head movements had little impact on a* rPPG. This comparison shows that the rPPG in CIELab space is more robust (e.g., resistant) to potential disturbance due to subject motion than that in RGB color space.

To further compare and quantify the performance of rPPG analysis in the CIELab and RGB color spaces, heart rate correlation with the electrocardiogram (ECG), signal-to-noise ratio, and error of peak-to-peak interval were determined.

Figure 8A:
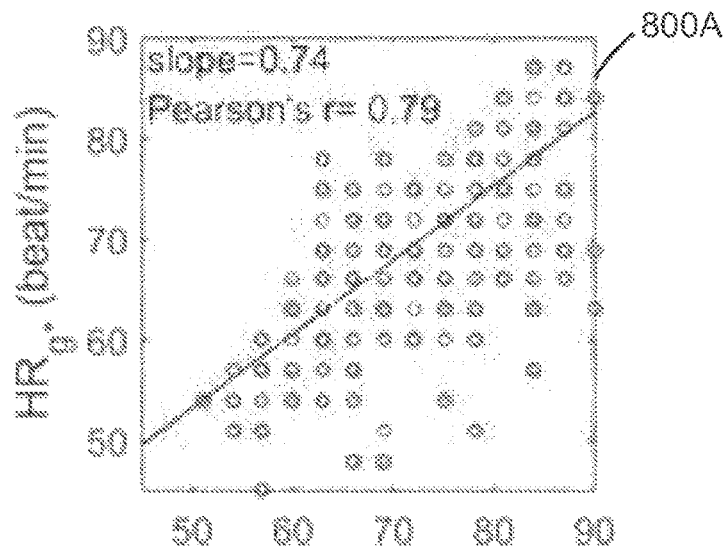
FIG. 8A is a scatter plot of heart rate detected with G* channel rPPG (RGB color space) and electrocardiography (ECG), overlaid with a linear fit, showing a linear correlation.
Figure 8B:
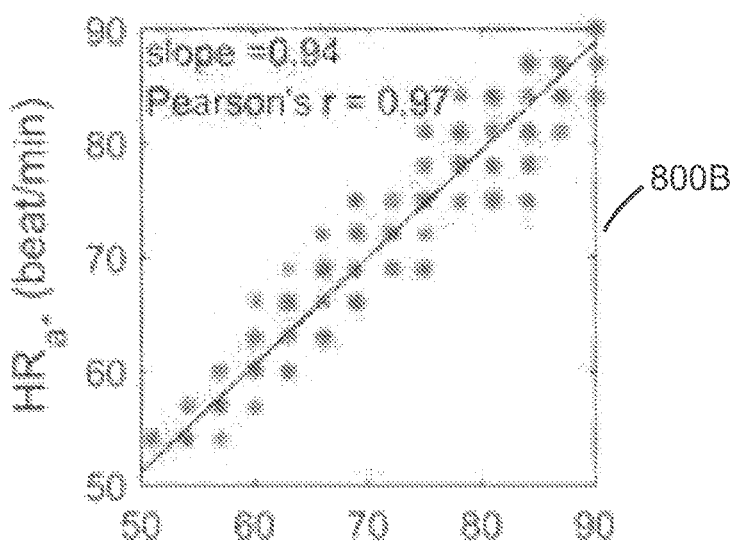
FIG. 8B is a scatter plot of heart rate detected with a* channel rPPG (CIELab color space) and ECG, overlaid with a linear fit, showing a linear correlation.

Heart rate (HR) is one of the most important physiological parameters, and the accuracy of the present rPPG method for tracking HR was validated using the ECG. The heartbeat events correspond to the peaks in rPPG, which were detected to determine HR within each window (20 s). FIG. 8A is a scatter plot 800A (also referred to herein as a correlation plot) of heart rate detected with G* channel rPPG (RGB color space) and electrocardiography (ECG), overlaid with a linear fit, showing a linear correlation. FIG. 8B is a scatter plot 800B (also referred to herein as a correlation plot) of heart rate detected with a* channel rPPG (CIELab color space) and ECG, overlaid with a linear fit, showing a linear correlation. The correlation plot 800A in FIG. 8A for G* channel rPPG has a slope of 0.74 with a Pearson value (r) of 0.79. In contrast, the correlation plot 800B in FIG. 8B for a* channel rPPG has a slope of 0.94 with r=0.97, which is significantly better than the rPPG signals in RGB color space.

Figure 9:
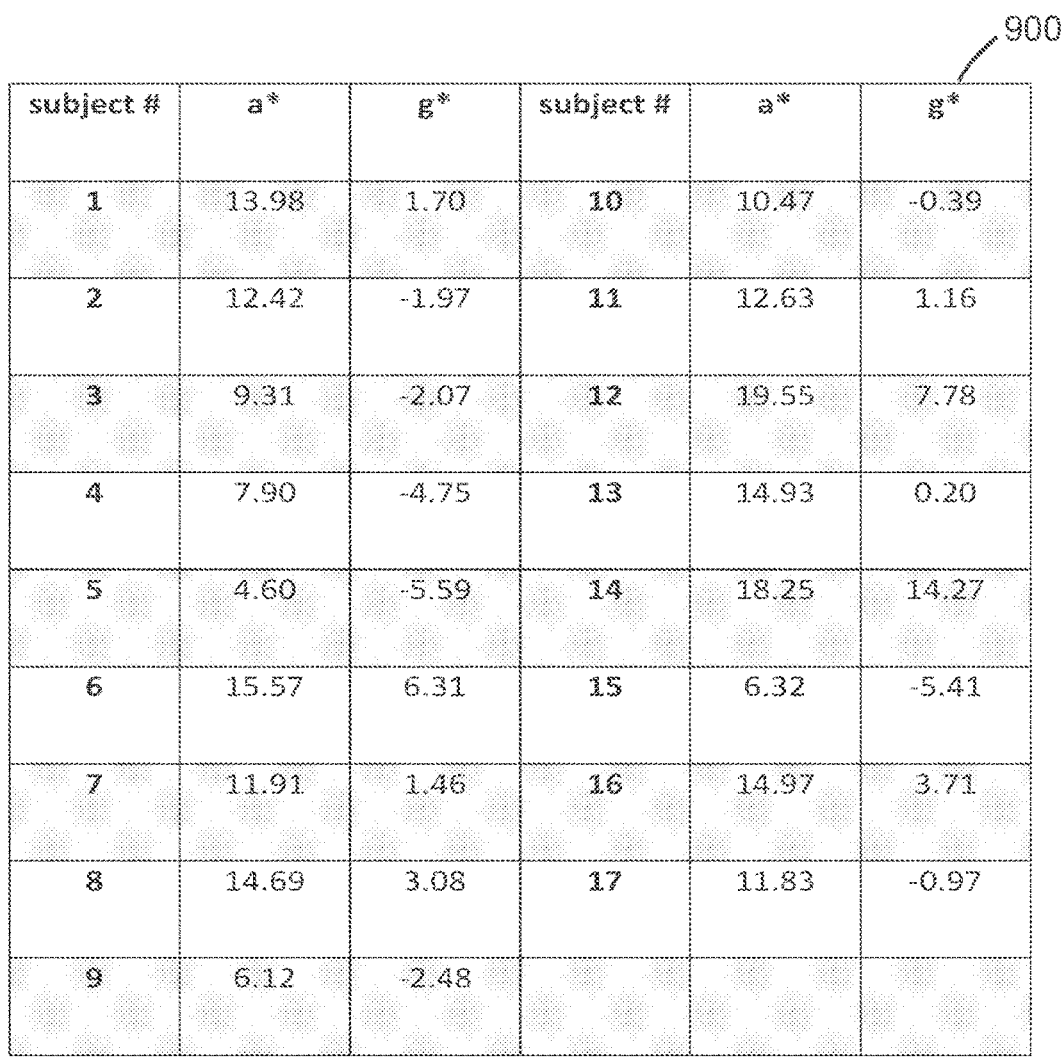
FIG. 9 is a table showing average signal-to-noise ratio values (SNRs) of a* channel rPPG and G* channel rPPG for each of 17 subjects.
Figure 10:
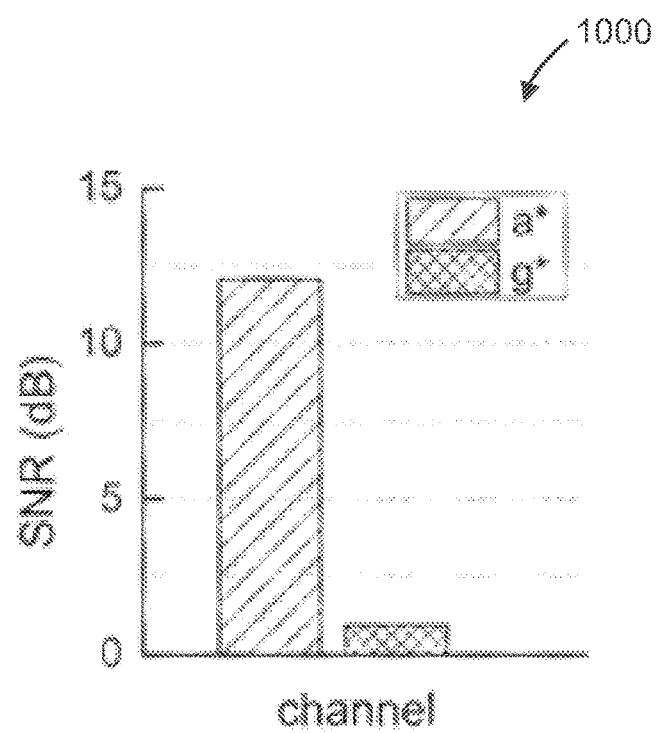
FIG. 10 is a bar chart comparing average SNRs of all 17 subjects of FIG. 9 for rPPG signals from channels a* and G* of the same subjects.

The signal-to-noise ratio (SNR) of the rPPG signals obtained in RGB and CIELab color spaces was evaluated using the following definition of SNR:

$$SNR = 10\log_{10}\left\{\frac{\sum_{f=0.7}^{4}(U_t(f)\hat{S}(f))^2}{\sum_{f=0.7}^{4}(1-U_t(f)\hat{S}(f))^2}\right\} \quad (7)$$

where $\hat{S}(f)$ is the spectrum of the pulse signal (f is frequency), $U_t(f)$ is a binary template window, which is 1 within two frequency windows (one around the fundamental frequency ($f_{HR}$) ([$f_{HR}$−0.2, $f_{HR}$+0.2]), and the other around the first harmonics ([$2f_{HR}$−0.2, $2f_{HR}$+0.2])), and 0 outside of the two frequency windows. See de Haan, G. and V. Jeanne, *Robust Pulse Rate From Chrominance-Based rPPG*, IEEE Transactions on Biomedical Engineering, 2013, 60(10): p. 2878-2886, the disclosure of which is hereby incorporated herein by reference in its entirety. The SNR analysis results for all 17 subjects are summarized in table 900 in FIG. 9. More specifically, the table 900 in FIG. 9 shows average (SNR) values of a* rPPG and G* rPPG for each of the 17 subjects. Despite the variability among different subjects, the SNRs for the rPPG from CIELab (a* rPPG) are consistently better than those for the rPPG from RGB color space (G* rPPG). The average SNR of all the subjects calculated from a* rPPG is 12, which is ten times higher than the SNR calculated from G* rPPG as shown in FIG. 10. More specifically, FIG. 10 is a bar chart 1000 comparing average SNRs (dB) of all 17 subjects for rPPG signals from a* and G* channels.

Figure 11A:
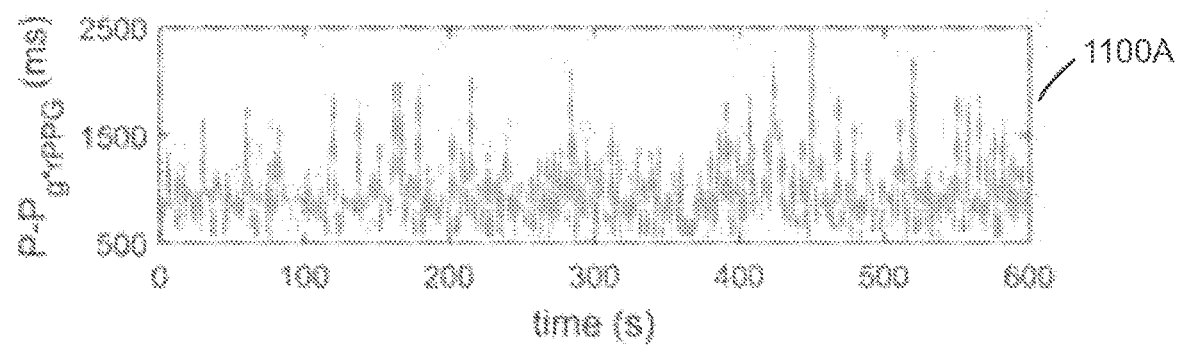
FIG. 11A is a line chart showing a peak-to-peak (P-P) interval sequence from G* channel rPPG.
Figure 11B:
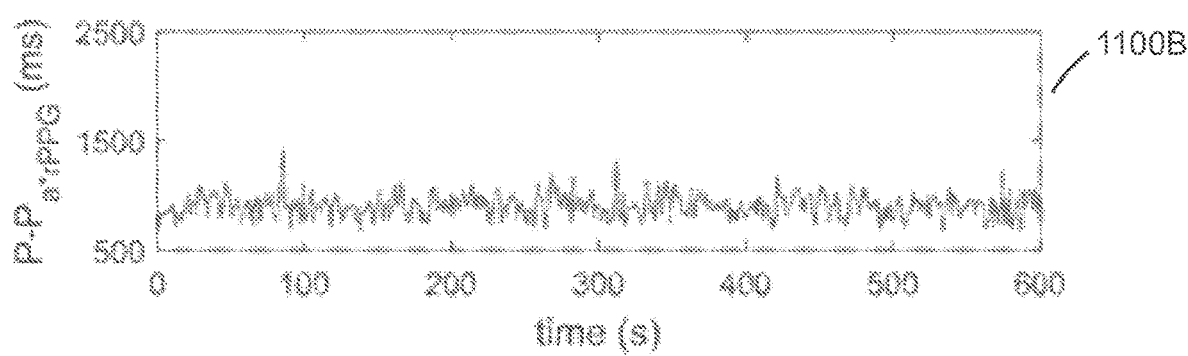
FIG. 11B is a line chart showing a P-P interval sequence from a* channel rPPG for the same timeframe as FIG. 11A.
Figure 11C:
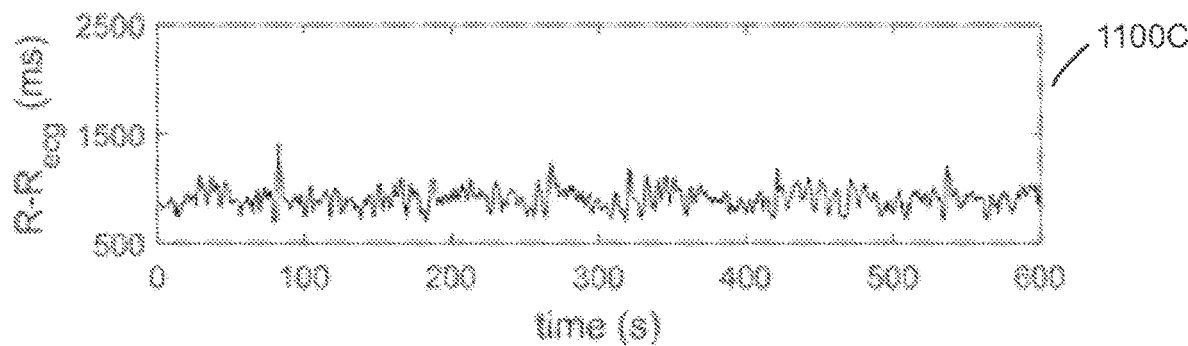
FIG. 11C is a line chart showing a recorded R wave-to-R wave (R-R) interval sequence from ECG for the same timeframe as FIGS. 11A and 11B.

Peak-to-peak (P-P) interval is another metric to evaluate the performance of the CIELab color space method. P-P interval detects the time period between two adjacent peaks, which is used to evaluate heart rate variability. The P-P interval sequence was aligned with the simultaneously recorded R wave-to-R wave (R-R) interval sequence in ECG. FIGS. 11A and 11B show typical examples of P-P interval sequences calculated from G* rPPG and a* rPPG, and FIG. 11C provides a comparison for these P-P interval sequences with R-R intervals from the simultaneously recorded ECG. More specifically, FIG. 11A is a line chart showing a P-P interval sequence 1100A from G* channel rPPG, FIG. 11B is a line chart showing a P-P interval sequence 1100B from a* channel rPPG for the same timeframe as FIG. 11A, and FIG. 11C is a line chart showing a R-R interval sequence 1100C from the ECG for the same timeframe as FIGS. 11A and 11B. Compared with the P-P interval sequence 1100A from G* channel rPPG, the P-P interval sequence 1100B from a* channel rPPG matches that of ECG (R-R interval sequence 1100C) much better. FIG. 12 summarizes the errors between the P-P intervals from the rPPG signals and the R-R intervals from the reference ECG. More specifically, FIG. 12 is a table 1200 showing the difference between P-P intervals of a* rPPG and the R-R intervals of the ECG and comparing that with the difference between P-P intervals of G* rPPG and the R-R intervals of the ECG. The average error between a* rPPG and ECG for all the subjects is 41.4 ms, while the average error between G* rPPG and ECG is 95.9 ms.

Figure 13:
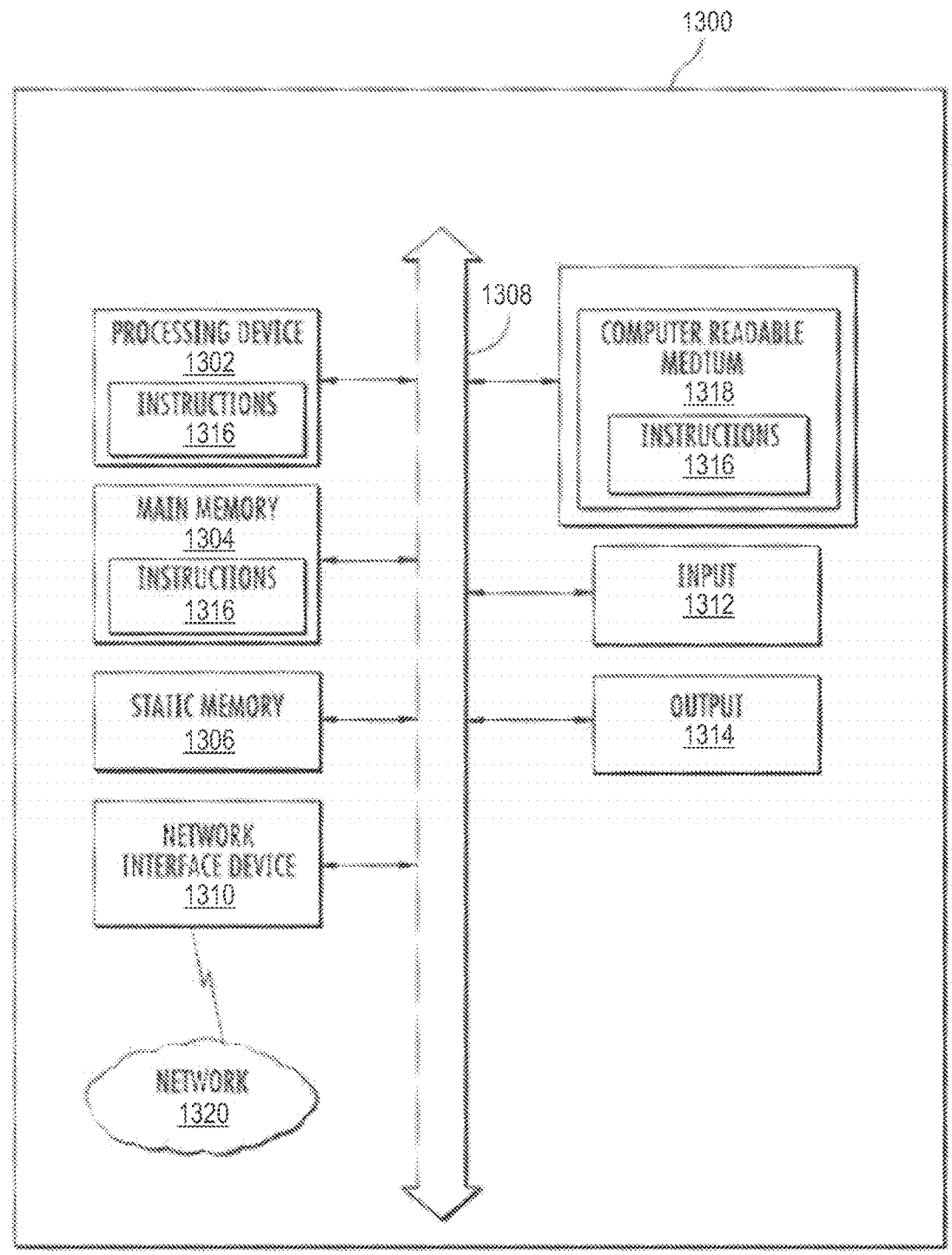
FIG. 13 is a schematic diagram of one embodiment of a computer system for monitoring of rPPG in a converted color space.

FIG. 13 is a schematic diagram representation of a computer system 1300 that could be employed in any of the above embodiments for monitoring of rPPG in a converted color space. The computer system 1300 is configured to execute instructions from an exemplary computer-readable medium to perform these and/or any of the functions or processing described herein.

The computer system 1300 may be connected (e.g., networked) to other machines in a LAN, an intranet, an extranet, or the Internet. While only a single processing device 1302 is illustrated, the term "device" shall also be taken to include any collection of devices that individually or jointly execute a set (or multiple sets) of instructions to perform any one or more of the methodologies discussed herein. The computer system 1300 may be or include a circuit or circuits implemented in or one an electronic board, such as a printed circuit board (PCB), a server, a personal computer, a desktop computer, a laptop computer, a personal digital assistant (PDA), a computing pad, a mobile device, or any other device, and may represent, for example, a server or a computer associated with a user.

The exemplary computer system 1300 in this embodiment includes a processing device or processor 1302, a main memory 1304 (e.g., read-only memory (ROM), flash memory, dynamic random access memory (DRAM), such as synchronous DRAM (SDRAM), etc.), and a static memory 1306 (e.g., flash memory, static random access memory (SRAM), etc.), which may communicate with each other via a data bus 1308. Alternatively, the processing device 1302 may be connected to the main memory 1304 and/or static memory 1306 directly or via some other connectivity means. The processing device 1302 may be a controller, and the main memory 1304 or static memory 1306 may be any type of memory.

In certain embodiments, the processing device 1302 may represent one or more general-purpose processing devices, such as a microprocessor, central processing unit, or the like. More particularly, the processing device 1302 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. In certain embodiments, the processing device 1302 may represent one or more application-specific processing devices, such as an application-specific integrated circuit (ASIC). The processing device 1302 is configured to execute processing logic embodied in instructions for performing the operations and steps discussed herein.

The computer system 1300 may further include a network interface device 1310. The computer system 1300 also may or may not include an input 1312, configured to receive input and selections to be communicated to the computer system 1300 when executing instructions. The computer system 1300 also may or may not include an output 1314 (including but not limited to a display, a video display unit (e.g., a liquid crystal display (LCD) or a cathode ray tube (CRT))), an alphanumeric input device (e.g., a keyboard), and/or a cursor control device (e.g., a mouse).

The computer system 1300 may or may not include a data storage device that includes instructions 1316 stored in a computer readable medium 1318. The instructions 1316 may also reside, completely or at least partially, within the main memory 1304 and/or within the processing device 1302 during execution thereof by the computer system 1300, the main memory 1304 and the processing device 1302 also constituting computer-readable medium. The instructions 1316 may further be transmitted or received over a network 1320 via the network interface device 1310.

While the computer readable medium 1318 is shown in an exemplary embodiment to be a single medium, the term "computer readable medium" should be taken to include a single medium or multiple media (e.g., a centralized or distributed database, and/or associated caches and servers) that store the one or more sets of instructions. The term "computer readable medium" shall also be taken to include any medium that is capable of storing, encoding, or carrying a set of instructions for execution by the processing device and that cause the processing device to perform any one or more of the methodologies of the embodiments disclosed herein. The term "computer readable medium" shall accordingly be taken to include, but not be limited to, solid-state memories, optical medium, and magnetic medium.

Upon reading the foregoing description in light of the accompanying drawing figures, those skilled in the art will understand the concepts of the disclosure and will recognize applications of these concepts not particularly addressed herein. Those skilled in the art will recognize improvements and modifications to the preferred embodiments of the present disclosure. All such improvements and modifications are considered within the scope of the concepts disclosed herein and the claims that follow.

What is claimed is:

1. A remote photoplethysmography (rPPG) system for monitoring by a computer system of at least one physiological parameter of a living body from image data, the rPPG system comprising a processor subsystem to:
    electronically receive, at the computer system, a first image data set from an optical imaging element, the first image data set being representative of a series of consecutive images of at least a portion of the living body;
    convert, by the computer system, the first image data set from a first color space to a second color space to generate a second image data set including a* channel data comprising a chromatic component corresponding to a chromaticity value defined between a green chromatic value and a red chromatic value, wherein the second color space is a perceptually uniform color space such that the chromatic component of the a* channel data is independent of an illumination of the series of consecutive images;
    process, by the computer system, the a* channel data to monitor at least one physiological parameter of the living body;
    automatically determine, by the computer system, a region of interest (ROI) of the living body in the first image data set and tracking, by the computer system, the ROI through at least some consecutive images of the series of consecutive images;
    initialize, by the computer system, the ROI based on a first image of the series of consecutive images; and
    reinitialize, by the computer system, the ROI after a predetermined number of images of the series of consecutive images.

2. The rPPG system of claim 1, wherein the first color space comprises an RGB color space.

3. The rPPG system of claim 1, wherein the second color space comprises:
    a CIELab color space, wherein the a* channel data is descriptive of a variation in color of the living body over a period of time between a green chromatic value and a red chromatic value.

4. The rPPG system of claim 1, wherein the at least one physiological parameter comprises at least one of breathing pattern, respiration rate, or heart rate.

5. The rPPG system of claim 1, wherein the computer system removes one or more consecutive images of the series of consecutive images if a number of identified feature points in the ROI in the one or more consecutive images is below a predetermined threshold.

6. The rPPG system of claim 1, wherein the computer system converts the first image data set from the first color space to the second color space by:
    converting the first image data set from the first color space to an intermediate color space to generate an intermediate image data set; and
    converting the intermediate image data set from the intermediate color space to the second color space to generate the second image data set;

wherein the intermediate color space is an XYZ color space.

7. A method for remote photoplethysmography (rPPG) monitoring by a computer system, the method comprising:
electronically receiving, at the computer system, a first image data set from an optical imaging element, the first image data set being representative of a series of consecutive images of at least a portion of a living body;
converting, by the computer system, the first image data set from a first color space to a second color space to generate a second image data set including a* channel data comprising a chromatic component corresponding to a chromaticity value defined between a green chromatic value and a red chromatic value, wherein the second color space is a perceptually uniform color space such that the chromatic component of the a* channel data is independent of an illumination of the series of consecutive images;
processing, by the computer system, the a* channel data to monitor at least one physiological parameter of the living body;
automatically determining, by the computer system, a region of interest (ROI) of the living body in the first image data set, and tracking, by the computer system, the ROI through at least some consecutive images of the series of consecutive images; and
removing, by the computer system, one or more consecutive images of the series of consecutive images if a number of identified feature points in the ROI in the one or more consecutive images is below a predetermined threshold.

8. The method of claim 7, wherein the first color space comprises an RGB color space.

9. The method of claim 7, wherein the second color space comprises:
a CIELab color space, wherein the a* channel data is descriptive of a variation in color of the living body over a period of time between a green chromatic value and a red chromatic value.

10. The method of claim 7, wherein the at least one physiological parameter comprises at least one of breathing pattern, respiration rate, or heart rate.

11. The method of claim 7, further comprising automatically determining, by the computer system, a region of interest (ROI) of the living body in the first image data set, and tracking, by the computer system, the ROI through at least some consecutive images of the series of consecutive images.

12. The method of claim 11, further comprising:
initializing, by the computer system, the ROI based on a first image of the series of consecutive images; and
reinitializing, by the computer system, the ROI after a predetermined number of images of the series of consecutive images.

13. The method of claim 7, wherein the step of converting the first image data set from the first color space to the second color space by:
converting the first image data set from the first color space to an intermediate color space to generate an intermediate image data set; and
converting the intermediate image data set from the intermediate color space to the second color space to generate the second image data set;

wherein the intermediate color space is an XYZ color space.

14. A non-transitory computer readable medium comprising program instructions for execution by a processor of a computer system to cause the computer system to perform the following steps:
electronically receive, at the computer system, a first image data set from an optical imaging element, the first image data set being representative of a series of consecutive images of at least a portion of a living body;
convert, by the computer system, the first image data set from a first color space to a second color space to generate a second image data set including a* channel data comprising a chromatic component corresponding to a chromaticity value defined between a green chromatic value and a red chromatic value, wherein the second color space is a perceptually uniform color space such that the chromatic component of the a* channel data is independent of an illumination of the series of consecutive images;
process, by the computer system, the a* channel data to monitor at least one physiological parameter of the living body;
automatically determine, by the computer system, a region of interest (ROI) of the living body in the first image data set and tracking, by the computer system, the ROI through at least some consecutive images of the series of consecutive images;
initialize, by the computer system, the ROI based on a first image of the series of consecutive images; and
reinitialize, by the computer system, the ROI after a predetermined number of images of the series of consecutive images.

15. The non-transitory computer readable medium of claim 14, wherein the first color space comprises an RGB color space.

16. The non-transitory computer readable medium of claim 14, wherein the second color space comprises:
a CIELab color space, wherein the a* channel data is descriptive of a variation in color of the living body over a period of time between a green chromatic value and a red chromatic value.

17. The non-transitory computer readable medium of claim 14, wherein the at least one physiological parameter comprises at least one of breathing pattern, respiration rate, or heart rate.

18. The non-transitory computer readable medium of claim 14, further comprising removing, by the computer system, one or more consecutive images of the series of consecutive images if a number of identified feature points in the ROI in the one or more consecutive images is below a predetermined threshold.

19. The non-transitory computer readable medium of claim 14, further comprising converting the first image data set from the first color space to the second color space by:
converting the first image data set from the first color space to an intermediate color space to generate an intermediate image data set; and
converting the intermediate image data set from the intermediate color space to the second color space to generate the second image data set;
wherein the intermediate color space is an XYZ color space.

* * * * *